(12) United States Patent
Weinberg et al.

(10) Patent No.: US 7,468,138 B2
(45) Date of Patent: Dec. 23, 2008

(54) FLEXURAL PLATE WAVE SENSOR

(75) Inventors: Marc S. Weinberg, Needham, MA (US);
Brian Cunningham, Lexington, MA (US); Eric Hildebrant, Watertown, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 11/496,229

(22) Filed: Jul. 31, 2006

(65) Prior Publication Data

US 2006/0260108 A1    Nov. 23, 2006

Related U.S. Application Data

(62) Division of application No. 10/675,398, filed on Sep. 30, 2003, now Pat. No. 7,109,633.

(51) Int. Cl.
*H04R 17/00* (2006.01)

(52) U.S. Cl. .......................................... 216/2; 29/25.35
(58) Field of Classification Search ........................ None
See application file for complete search history.

(56) References Cited

U.S. PATENT DOCUMENTS

| 5,852,337 A * | 12/1998 | Takeuchi et al. ............. 310/328 |
| 2003/0066348 A1 * | 4/2003 | Cunningham ............. 73/382 R |

* cited by examiner

*Primary Examiner*—Allan Olsen
(74) *Attorney, Agent, or Firm*—Iandiorio Teska & Coleman

(57) ABSTRACT

A method for manufacturing a flexural plate wave sensor, the method including the steps of depositing an etch-stop layer over a substrate, depositing a membrane layer over said etch stop layer, depositing a piezoelectric layer over said membrane layer, forming a comb pattern with drive teeth which span across an entire length of the piezoelectric layer on said piezoelectric layer, etching a cavity through the substrate, the cavity having substantially parallel interior walls, and removing a portion of the etch stop layer between the cavity and the membrane layer to expose a portion of the membrane layer.

4 Claims, 22 Drawing Sheets

FIG. 16A

```
 1: %MATLAB CODE FOR FPW CHEMICAL SENSOR MODAL FREQUENCY RESPONSE
 2: %
 3: %VARMODEEIG.M  PARAMETERS FOR MICROCANARY
 4: %PLATE WAVE RESONATOR DYNAMIC MODEL
 5: %BASED ON FPW5 EXPANDED TO ARBITRARY NUMBER OF MODES BY ELI WEINBERG 7/19/99
 6: %SEPTEMBER, 1999. CLOSER SCALING AND DIFFERENTIAL SENSE READING ADDED BY MSW.
 7: %SEPARATE DRIVE AND SENSE INPUTS
 8: %FIRST CODED 10/13/97
 9: %    9/20/02 Calculate eigenvalues (photosensitivity investigation) difference from mechanical only
10: %LATEST RUN 9/20/02
11:
12: % 11/13/01 ATTEMPT THE CHEMICAL SENSOR Q = 100 CASES
13: clear, format compact, format short e, i=sqrt (-1);
14: diary c:\matlab6p1\mw\varmodec.dia
15: rd = 50/4      %xxx
16:                %EXTERNAL DRIVE RESISTANCE.  THE FACTOR OF FOUR ACCOUNTS FOR THE N=2
17:                %TRANSFORMERS AND THE FACT THAT CD IS FOR +/- DRIVE IN PARALLEL.
18: rs = 100/2     %xxx  %ONE HALF EXTERNAL SENSE RESISTANCE (ohm)
19:                %THE FACTOR OF TWO ACCOUNTS FOR CS IS +/- DRIVE IN PARALLEL.
20:                %GAINS BEFORE SOURCE VOLTAGE IS APPLIED TO FPW
21: gamp=1         %INPUT AMPLIFIER-BOTH INPUT AND REFERENCE LEGS HAVE SAME GAIN
22: ginst = 190    %INSTRUMENTATION AMPLIFIER GAIN-
23:                %Completely differential amplifier with 10X second stage
24: gtran= 0.5     %TRANSFORMER GAIN
25: %VALUES FOR ALM = 0.5 MICRON, SI = TWO MICRONS
26: mp=2.47e-6     %xxx MASS PER UNIT LENGTH (KG/M)
27: dd = 8.781e-11 %STRUCTURAL RIGIDITY (N/M^2)
28: %q = 400 when bb - 1.033      %xxx
29: bb = 1.033             %xxx damping (N-s/m^2)
30: l = 0.0015     %LENGTH OF DIAPHRAGM (m)
31: ld = 3.750001E-5*19    %LENGTH OF THE DRIVE TRANSDUCER
32: ls = 3.750001E-5*19    %LENGTH OF THE SENSE TRANSDUCER
33: md=38                  %NUMBER OF HALF PERIODS IN TRANDUCER
34: ms=38                  %NUMBER OF HALF PERIODS IN TRANSDUCER
35: pd = 2*ld/md           %PITCH OF DRIVE FINGERS (M)
```

FIG. 16B

```
36:     ps = 2*ls/ms          %PITCH OF SENSE FINGERS (M)
37:     %CALCULATE THE MODAL FORCING FUNCTION
38:     phi= 0        %PHASE OF EIGENFREQUENCY (0 FOR PINNED, PI/4 FOR BUILT-IN)
39:     thetad= 0     %PHASE OF TRANSDUCER (radians)
40:     thetas = 0
41:     xd=0          %STARTING POSITION FOR FORCING COMBS
42:     xs=1-ls-xd    %STARTING POSITION OF TRANSDUCER 20
43:     %BEWARE CHANGING XD TO ADJUST TOLERENCES.
44:     %SCALE FACTOR FOR LENGTH OF SENDER OR RECEIVER COMB
45:     %MODEINT IS MSW FUNCTION BASED ON MACSYMA INTEGRATION
46:
47:     nmode=input('Enter number of modes  ')
48:     model=input('Enter number of first mode in model  ')
49:
50:     for c0=1:nmode
51:         n(c0)=(model-1+c0);
52:     end   %MODE NUMBER, ROUGHLY NUMBER OF HALF WAVE LENGTHS
53:
54:
55:
56:     alph = 0.004874/1.676e5^2
57:             %piezo coupling coefficient for 100% transducer length (coul/m)
58:     gamm = 9.39e-11*1.676e5^4        %piezo coupling coefficient  (m/V)
59:
60:     for c1 = 1:nmode;
61:         pc(c1,1)=modeint(n(c1),md,l,ld,phi,thetad,xd);
62:         pc(c1,2)=modeint(n(c1),ms,l,ls,phi,thetas,xs);
63:         lam(c1)=n(c1)*pi/l; %eigenvalue of plate motion  (1/m)
64:         gammad(c1)=gamm*pc(c1,1)/lam(c1)^4;
65:         gammas(c1)=gamm*pc(c1,2)/lam(c1)^4;
66:         alphad(c1)=alph*lam(c1)^2*pc(c1,1);
67:         alphas(c1)=alph*lam(c1)^2*pc(c1,2);
68:         wn(c1)=sqrt(dd/mp)*lam(c1)^2;   %eigenfrequency (rad/s)
69:         damping(c1) = bb;                %mode damping (N-s/m^2)
70:         k(c1) = mp*wn(c1)^2;             %mode stiffness (N/m^2)
71:         checkalpha(c1) = 1-gammad(c1)*k(c1)*0.5*1/alphad(c1);
```

```
72:    end
73:    pc,wn,gammad,gammas,alphad,alphas,checkalpha
74:
75:    cs = 7.567e-11*ls/1    %CAPACITANCE FROM SENSE COMBS TO GROUND, 2 POLES (F)
76:                           %EQUAL TO THAT CALCULATED IN TABLE 1. STRAYS MAY ADD MORE.
77:    cd = 7.567e-11*ld/1    %DRIVE CAPACITANCE (F)
78:    rfb=rs*ginst           %SENSE AXIS RESISTOR AND INSTRUMENTATION AMPLIFIER
79:
80:    %ENTER THE COEFFICIENTS OF THE DERIVATIVES
81:    %STATES ARE [QD,QS,V1,X1,V2,X2,V3,X3]
82:    ml=zeros(2+2*nmode, 2+2*nmode);
83:    mra=zeros(2+2*nmode, 2+2*nmode);
84:    ml(1,1)=(cd*rd);
85:    ml(2,2)=cs*rs;
86:    mra(1,1)=-1;
87:    mra(2,2)=-1;
88:
89:    for c2=1:nmode
90:        ml(2*c2+1, 2*c2+1)=mp;
91:        ml(2*c2+2, 2*c2+2)=1;
92:        ml(2*c2+1, 1)=rd*k(c2)*gammad(c2);
93:        ml(2*c2+1, 2)=rs*k(c2)*gammas(c2);
94:
95:        mra(2*c2+1, 2*c2+1)=-damping(c2);
96:        mra(2*c2+1, 2*c2+2)=-k(c2);
97:        mra(2*c2+2, 2*c2+1)=1;
98:        mra(1, 2*c2+2)=alphad(c2);
99:        mra(2, 2*c2+2)=alphas(c2);
100:   end
101:
102:   %ENTER COEFFICIENTS OF DRIVE VOLTAGE
103:   mrb=zeros(2*nmode+2, 1);
104:   mrb(1)=cd;
105:   for c3=1:nmode
106:       mrb(2*c3+1)=k(c3)*gammad(c3);
107:   end
```

*FIG. 16C*

```
108:    %ml, mra, mrb
109:
110:    %SET UP THE STATE MATRICES
111:    invml=inv(ml);
112:    checkinvml=invml*ml
113:    a=invml*mra
114:    b=invml*mrb
115:    [evec,eval]=eig(a);
116:    damp(eval)
117:    %eval
118:    %evec
119:
120:    %PICK OUT THE DIFFERENCE IN THE EIGENFREQUENCIES
121:    yy=sort(damp(eval));  %PLACE THE EIGENVALUES IN ORDER. CHECK THAT THE POLES CORRESPONDING TO THE
122:                          %RC ARE HIGHER THAN THE MECHANICAL POLES
123:    for ii = 1:nmode
124:        wncl(ii)=yy(2*ii-1);  %MAKE THE VECTORS OF DIFFERENT LENGTHS SIMILAR AND OMIT THE TWO FASTEST POLES
125:    end
126:    wndiff=wncl-wn         %SHIFT FROM MECHANICAL RESONANCES TO CLOSED LOOP
127:
128:    %OUTPUTS ARE AMPLITUDE, SENSE PREAMPLIFIER OUTPUT, AND INPUT CHARGE THROUGH RD
129:    %WITH GIN = 1 INPUT IS INPUT TO 10X AMPLIFIER WHICH IS MEASURED BY
130:    %ANALYZER
131:    gin = 1       %SOURCE TO PREAMP INPUT
132:    c=zeros(3, 2+2*nmode);
133:    for c4=1:nmode
134:        c(1, 2*c4+2)=1;
135:        c(2, :)=a(2, :)*rfb;
136:        c(3, 1)=.5;
137:    end
138:    c=c*gamp*gtran*gin
139:    d=[0;b(2,:)*rfb; 0]*gamp*gtran*gin
140:    %w=logspace(7,9,200);
```

```
142:  nw=1001
143:  dw=(1.1*wn(nmode)-0.9*wn(1))/(nw-1);
144:  w=[0.9*wn(1):dw:1.1*wn(nmode)];
145:  wmax=w(length(w))
146:  [m1,p1]=unbode(a,b,c,d,1,w);
147:  xmax = max(m1(:,1))
148:  vmax = max(m1(:,2))
149:  figure(1),clf,subplot(2,1,1)
150:  semilogy(w,m1(:,2)),grid,xlabel('frequency (rad/s)')
151:  ylabel('sense out  (V/V)'),axis([w(1),wmax,0.01,max(m1(:,2))])
152:  title('SENSE AXIS PREAMPLIFIER OUTPUT')
153:  subplot(2,1,2)
154:  plot(w,p1(:,2)),grid,xlabel('frequency (rad/s)'), ylabel('phase (deg)')
155:  figure(2),clf,subplot(2,1,1)
156:  semilogy(w,m1(:,1)),grid,xlabel('frequency (rad/s)')
157:  ylabel('amplitude (m/V)'),axis([w(1),wmax,0.01*max(m1(:,1),max(m1(:,1))])
158:  title('MOTION AMPLITUDE')
159:  subplot(2,1,2)
160:  plot(w,p1(:,1)),grid,xlabel('frequency (rad/s)'), ylabel('phase (deg)')
161:  figure(3),clf,subplot(2,1,1)
162:  semilogy(w,m1(:,3)),grid,xlabel('frequency (rad/s)')
163:  ylabel('charge (C/V)')
164:  title('DRIVE CHARGE')
165:  subplot(2,1,2)
166:  plot(w,p1(:,3)),grid,xlabel('frequency (rad/s)'), ylabel('phase (deg)')
167:  %[z,p,k,]=ss2zp(a,b,c,d,1) %OBTAIN THE POLES AND ZEROS OF TRANSFER FUNCTION
168:  diary off
169:
170:
```

```
1: function [pc]=modeint(n,m,l,lt,phi,theta,xo);
2: %FUNCTION TO OBTAIN THE MODAL FORCING FUNCTION NORMALIZED TO ONE
3: %DERIVED BY MACSYMA AND CODED 10/20/97
4: pc = -lt*sin(((pi*lt*n+pi*l*m)*xo-l*lt*theta-l*lt*phi+pi*lt^2.....
5:      *n+pi*l*lt*m)/(l*lt))/(pi*(lt*n+l*m))+lt*sin(((pi*lt*n+.....
6:      pi*l*m)*xo-l*lt*theta-l*lt*phi)/(l*lt))/(pi*(lt*n+l*m))+lt*.....
7:      sin(((pi*lt*n-pi*l*m)*xo+l*lt*theta-l*lt*phi+pi*lt^2*n-pi.....
8:      *l*lt*m)/(l*lt))/(pi*(lt*n-l*m))-lt*sin(((pi*lt*n-pi*l*m)*.....
9:      xo+l*lt*theta-l*lt*phi)/(l*lt))/(pi*(lt*n-l*m));
10:
```

*FIG. 16F*

Static Plate Deflections
for Sinusoidal Load

FLEXURAL PLATE WAVE SENSOR

RELATED APPLICATIONS

This application is a Divisional application of U.S. patent application Ser. No. 10/675,398, filed on Sep. 30, 2003 now U.S. Pat. No. 7,109,633, hereby incorporated by reference herein.

FIELD OF THE INVENTION

This invention relates generally to flexure plate wave sensors and more particularly to an improved comb pattern for a flexural plate wave sensor.

BACKGROUND OF THE INVENTION

A flexural plate wave (FPW) sensor includes a diaphragm or plate which is driven so it oscillates at frequencies determined by a comb pattern and the flexural plate geometry. The comb pattern is disposed over the flexural plate and establishes electric fields which interact with the plate's piezoelectric properties to excite motion. The eigenmodes describe the diaphragm displacements which exhibit spatially distributed peaks. Each eigenmode consists of n half sine periods along the diaphragm's length. A typical FPW sensor can be excited to eighty or more eigenmodes. In a typical FPW eigenmode, the plate deflection consists of many sinusoidal (or nearly sinusoidal) peaks.

Prior art flexure plate wave sensors typically include drive combs at one end of the plate and sense combs at the other end. The drive combs of these prior art devices typically cover only twenty-five to forty percent of the total length of the plate. When the number of drive teeth is small compared to the number of eigenmodes peaks, the small number of drive teeth can align with several eigenmodes. The result is that not only are the eigenmodes perfectly aligned with the comb teeth excited, but other eigenmodes are also excited. In signal processing and spectral analysis, this effect is known as leakage. A significant drawback of prior designs is that the increased number of eigenmodes excited in the FPW sensor produces a series of resonance peaks of similar amplitude and irregular phase which increases design complexity and the operation of the prior art flexure plate wave sensors.

Moreover, prior art flexural plate wave sensors utilize drive and sense combs at opposite ends of the flexural plate and rely on analysis based on an analogy to surface acoustic waves (SAW) wherein the waves propagate away from the drive combs and toward the sense combs and back reflections are regarded as interference. A distinct disadvantage of this analysis is that SAW theory does not account for numerous small peaks produced by the sensor resulting in calculated gains (e.g., peaks of similar magnitude) which are low and do not account for sharp phase drops seen with the peaks (e.g., irregular phase).

SUMMARY OF THE INVENTION

It is therefore an object of this invention to provide an improved flexural plate wave sensor.

It is a further object of this invention to provide such a sensor which reduces the number of eigenmodes excited in the flexural plate.

It is a further object of this invention to provide such a sensor which outputs a single pronounced peak, or a peak much larger than any of the other peaks.

It is a further object of this invention to provide such a sensor which outputs a distinct phase.

It is a further object of this invention to provide such a sensor which simplifies the operation and design of the sensor.

It is a further object of this invention to provide such a sensor which improves stability and performance of the sensor.

It is a further object of this invention to provide such a sensor which improves stability by eliminating erroneous readings due to interference created by mode hopping from other eigenmodes is eliminated.

This invention results from the realization that a truly effective and robust flexural plate wave sensor is achieved by utilizing a unique comb pattern over the flexural plate with drive teeth disposed across the entire length of the flexural plate and which, in one embodiment, are aligned with all the eigenmodes of the flexural plate resulting in the ability to reduce the number of eigenmodes excited in the plate and the output of a single pronounced peak with a distinct phase simplifying the operation and design of the flexural plate wave sensor.

This invention features a flexural plate wave sensor including a flexural plate having a length and a width, and a comb pattern over the flexural plate with drive teeth disposed across the entire length of the flexural plate to reduce the number of eigenmodes excited in the plate and thereby simplifying the operation and design of the flexure plate wave sensor. The sensor may include sense teeth disposed across the entire length of the flexure plate interleaved with the drive teeth. In one example, the sense teeth face in one direction and the drive teeth face in an opposite direction.

In one embodiment of this invention, the comb pattern is aligned with one eigenmode of the flexural plate thereby exciting one eigenmode in the plate. In one design, the comb pattern allows the sensor to output a single pronounced peak thereby improving the performance of the sensor. The comb pattern of this invention may also reduce a transfer function of the sensor to a single peak, or a peak much larger than any other peak. In one preferred embodiment, the drive teeth are aligned with the eigenmodes excited in the flexural plate. The sense teeth may also be aligned with the eigenmodes excited in the flexural plate. Typically, the comb pattern provides for establishing electric fields which interact with piezoelectric properties of the flexural plate to excite motion. The comb pattern may be made of a material chosen from the group consisting of copper, titanium-platinum-gold (TiPtAu) metal, titanium-platinum (TiPt), and aluminum. Typically, the comb pattern is approximately 0.1 μm thick and may include wire bond pad areas and ground contacts. In one design, the drive teeth are on the flexural plate. The sense teeth may also be on the flexural plate. Ideally, the drive teeth span across an entirety of the width of the flexural plate. The sense teeth may also span across an entirety of the width of the flexural plate.

The flexure plate wave sensor may include a base substrate, an etch stop layer disposed over the base substrate, a membrane layer disposed over the etch stop layer, a cavity disposed in the base substrate and the etch stop layer, thereby exposing a portion of the membrane layer, the cavity having substantially parallel interior walls, a piezoelectric layer disposed over the membrane layer and the comb pattern disposed over the piezoelectric layer. The piezoelectric layer may be formed from a material selected from the group consisting of aluminum nitrite, zinc oxide and lead zirconium titanate. The etch stop layer is typically formed from silicon dioxide. Ideally, the membrane layer is formed from silicon. In one example, the base substrate is formed from silicon.

In one design of this invention, the base substrate includes a silicon-on-insolator (SOI) wafer, which may include an upper surface of silicon forming the membrane layer bonded to an etch stop layer. In other examples, the piezoelectric transducer may be deposited over the upper surface of the epitaxial silicon. Ideally, grounding contacts to the epitaxial silicon are provided by etching an opening into the piezoelectric transducer. In one design, the comb pattern includes titanium-platinum-gold (TiPtAu) metal. The comb pattern typically includes interdigital metal electrodes, wire bond pad areas, and ground contacts. In an embodiment, the base substrate is approximately 380 μm thick, the upper epitaxial surface is approximately 2 μm thick, the layer of $SiO_2$ is approximately 1 μm thick, and the comb pattern is approximately 0.1 μm thick. The drive teeth may be approximately 300 to 2000 μm in length and the spacing between the drive teeth may be approximately 25 to 50 μm. Typically, the sense teeth are approximately 300 to 2000 μm in length and the spacing between the sense teeth is approximately 25 to 50 μm.

This invention further features a flexural plate wave sensor including a flexural plate having a length and a width, and a comb pattern over the flexural plate with drive and sense teeth disposed across the entire length of the flexural plate to reduce the number of eigenmodes excited in the plate and thereby simplifying the operation and design of the flexure plate wave sensor.

This invention also features a flexural plate wave sensor including a flexural plate having a length and a width, and a comb pattern over the flexural plate with first and second sets of drive teeth disposed across the entire length of the flexural plate to reduce the number of eigenmodes excited in the plate and thereby simplify the operation and design of the flexural plate wave sensor. In one embodiment the sensor includes first and second sets of sense teeth disposed across the entire length of the flexural plate. The first and second sets of drive teeth typically face in opposite directions. The first and second sets of sense teeth may face in opposite directions. In one design, the first and second sets of drive teeth are interleaved. The first and second sets of sense teeth may also be interleaved. The first and second sets of interleaved drive teeth may span the entire length and approximately fifty percent of the width of the flexural plate. The first and second sets of interleaved sense teeth may also span the entire length and approximately fifty percent of the width of the flexural plate. Typically, the first and second sets of drive teeth face in the same direction, and the first and second sets of sense teeth face in the same direction. In one embodiment, the first set of drive teeth is interleaved with the first set of sense teeth. The first set of drive teeth interleaved with the second set of sense teeth together may span approximately fifty percent of the width of the flexural plate. The second set of drive teeth may be interleaved with the second set of sense teeth. In other designs, the second set of drive teeth interleaved with the first set of sense teeth together may span approximately fifty percent of the width of the flexural wave plate.

This invention further features a flexural wave plate sensor including a flexural plate having a length and a width, and a comb pattern over the flexural plate with first and second sets of drive teeth disposed over the flexural plate. Typically, the first set of drive teeth span approximately seventy-five percent of the length of the flexural plate and the second set of drive teeth span approximately twenty-five percent of the length of the flexural plate. The comb pattern reduces the number of eigenmodes excited in the plate and thereby simplifying the operation and design of the flexural plate wave sensor.

In one embodiment, the sensor may include first and second sets of sense teeth disposed over the flexural plate, the first set of sense teeth spanning approximately seventy-five percent of the length of the flexural plate and the second set of sense teeth spanning approximately twenty-five percent of the length of the flexural plate. The first and second sets of sense teeth may be interleaved with the first and second sets of drive teeth. In one example, the first and second sets of drive teeth face one direction and the first and second sense teeth face in an opposite direction.

In other designs, the flexural plate wave sensor may include a flexural plate having a length, width, and a center, and a comb pattern over the flexural plate with first and second sets of drive teeth disposed across approximately fifty percent of the length of the flexural plate, each set of drive teeth spanning approximately an entirety of the width of the flexural plate at one end and curving toward the center of the flexural plate at approximately the center of the plate. Ideally, the comb pattern reduces the number of eigenmodes excited in the plate and thereby simplifying the operation and design of the flexural plate wave sensor. The sensor may also include first and second sets of sense teeth disposed across approximately fifty percent of the length of the flexural plate, each set of sense teeth spanning approximately an entirety of the width of the flexural plate and curving toward the center of the flexural plate at approximately a middle of the plate.

This invention also features a flexural wave plate sensor including a flexural plate having a length and a width, and a comb pattern over the flexural plate. The comb pattern may include drive teeth and sense teeth disposed over the flexural plate. The drive teeth may span approximately fifty percent of the length of the flexural plate. The sense teeth may span approximately the fifty percent of the length of the flexural plate. Ideally, the comb pattern reduces the number of eigenmodes excited in the plate and thereby simplifying the operation and design of the flexural plate wave sensor.

This invention further features a flexural wave plate sensor with a flexural plate having a length and a width, and a comb pattern over the flexural plate. The comb pattern may include a set of drive teeth and a set of sense teeth. The set of drive teeth and the set of sense teeth may be disposed over the flexural plate. The drive teeth may span approximately fifty percent of the length of the flexural plate, and the sense teeth may span approximately fifty percent of the length of the flexural plate. Ideally, the comb pattern reduces the number of eigenmodes excited in the plate and thereby simplifying the operation and design of the flexural plate wave sensor.

This invention also features a method for manufacturing a flexural plate wave sensor, the method including the steps of depositing an etch-stop layer over a substrate, depositing a membrane layer over the etch stop layer, depositing a piezoelectric layer over the membrane layer, forming a comb pattern with drive teeth which span across an entire length of the piezoelectric layer on the piezoelectric layer, etching a cavity through the substrate, the cavity having substantially parallel interior walls, and removing a portion of the etch stop layer between the cavity and the membrane layer to expose a portion of the membrane layer. The method of the manufacturing of a flexural plate wave sensor of this invention may further include the steps of etching a hole in the piezoelectric and forming a ground contact on the silicon membrane layer.

This invention further features a method for manufacturing a flexural plate wave sensor, the method including the steps of depositing an etch-stop layer over a substrate, depositing a membrane layer over the etch stop layer, depositing a piezoelectric layer over the membrane layer, forming a comb pattern on the piezoelectric layer, the comb pattern including drive and sense teeth which span an entire length of the membrane layer, forming a second transducer on the piezoelectric layer, spaced from the first transducer, etching a cavity through the substrate, the cavity having substantially parallel interior walls, removing the portion of the etch stop layer between the cavity and the membrane layer to expose a portion of the membrane layer, and depositing an absorptive coating on the exposed portion of the membrane layer.

The method of manufacturing a flexural plate of this invention may further include the steps of etching a hole in the piezoelectric and forming a ground contact on the silicon membrane layer.

BRIEF DESCRIPTION OF THE DRAWINGS

Other objects, features and advantages will occur to those skilled in the art from the following description of a preferred embodiment and the accompanying drawings, in which:

FIGS. 16A-16F are a listing of the MATLAB® code for a three-mode frequency response of one embodiment of the flexural plate wave sensor of this invention;

DISCLOSURE OF THE PREFERRED EMBODIMENT

Figure 1:
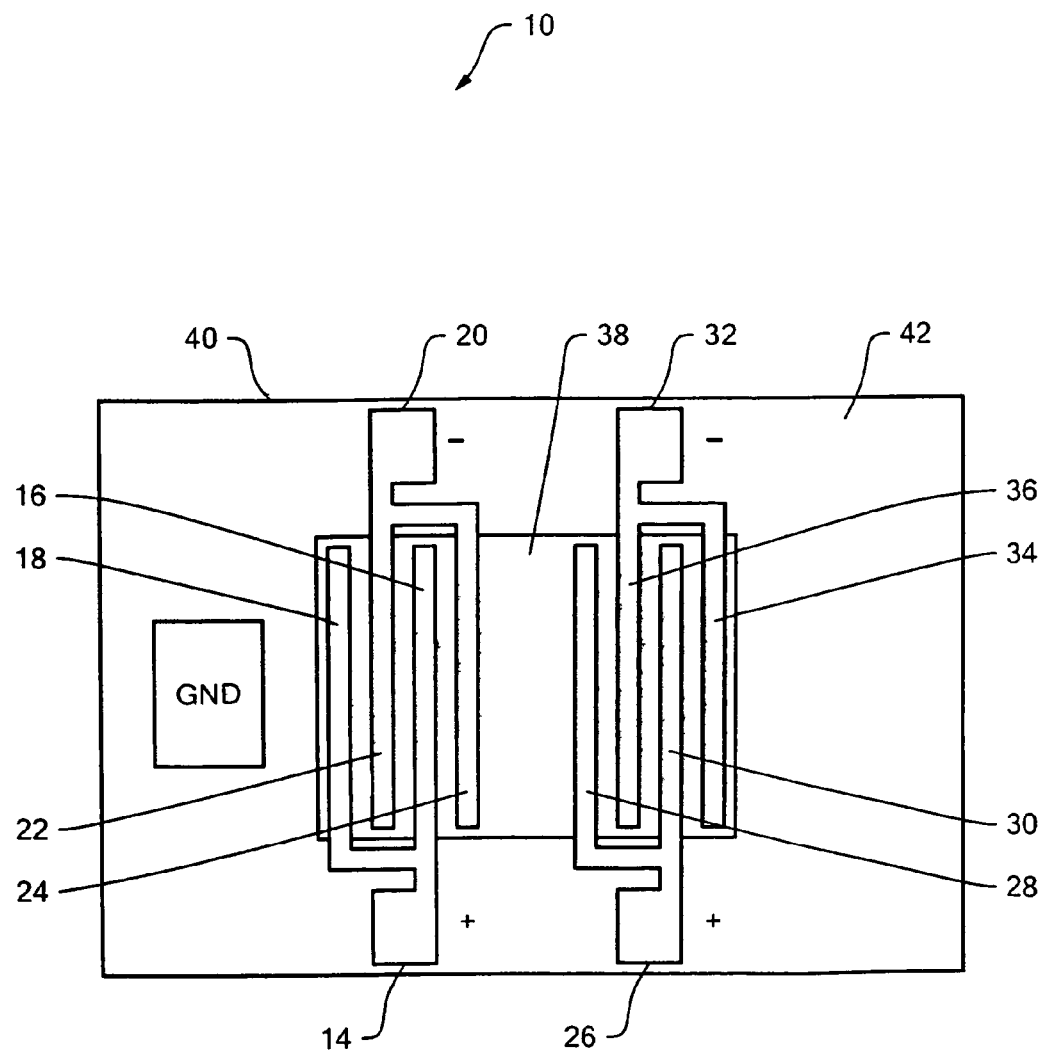
FIG. 1 is a schematic top view of a prior art flexural plate wave sensor showing drive and sense combs extending over approximately twenty-five to forty percent of the flexural wave plate.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

As discussed in the Background section above, prior art flexure plate wave sensor 10, FIG. 1 includes drive comb 14 with drive teeth 16 and 18 and drive comb 20 with drive teeth 22 and 24. Typically, drive combs 14 and 20 are driven at opposite polarity, e.g., drive comb 14 is driven at a positive polarity and drive comb 20 is driven at a negative polarity, to align with the positive and negative peaks of the eigenmodes.

As shown in FIG. 1, drive combs 14 and 20 are disposed over only approximately twenty-five to forty percent of the entire length of flexural plate 38. Because of the limited length extent of drive combs 14 and 20, there is a limited number of drive teeth, e.g., drive teeth 16, 18, 22, and 24. As discussed in the Background section above, when the number of drive teeth is small compared to the number of eigenmode peaks of the flexural plate 38, several eigenmodes will be excited.

Figure 2:
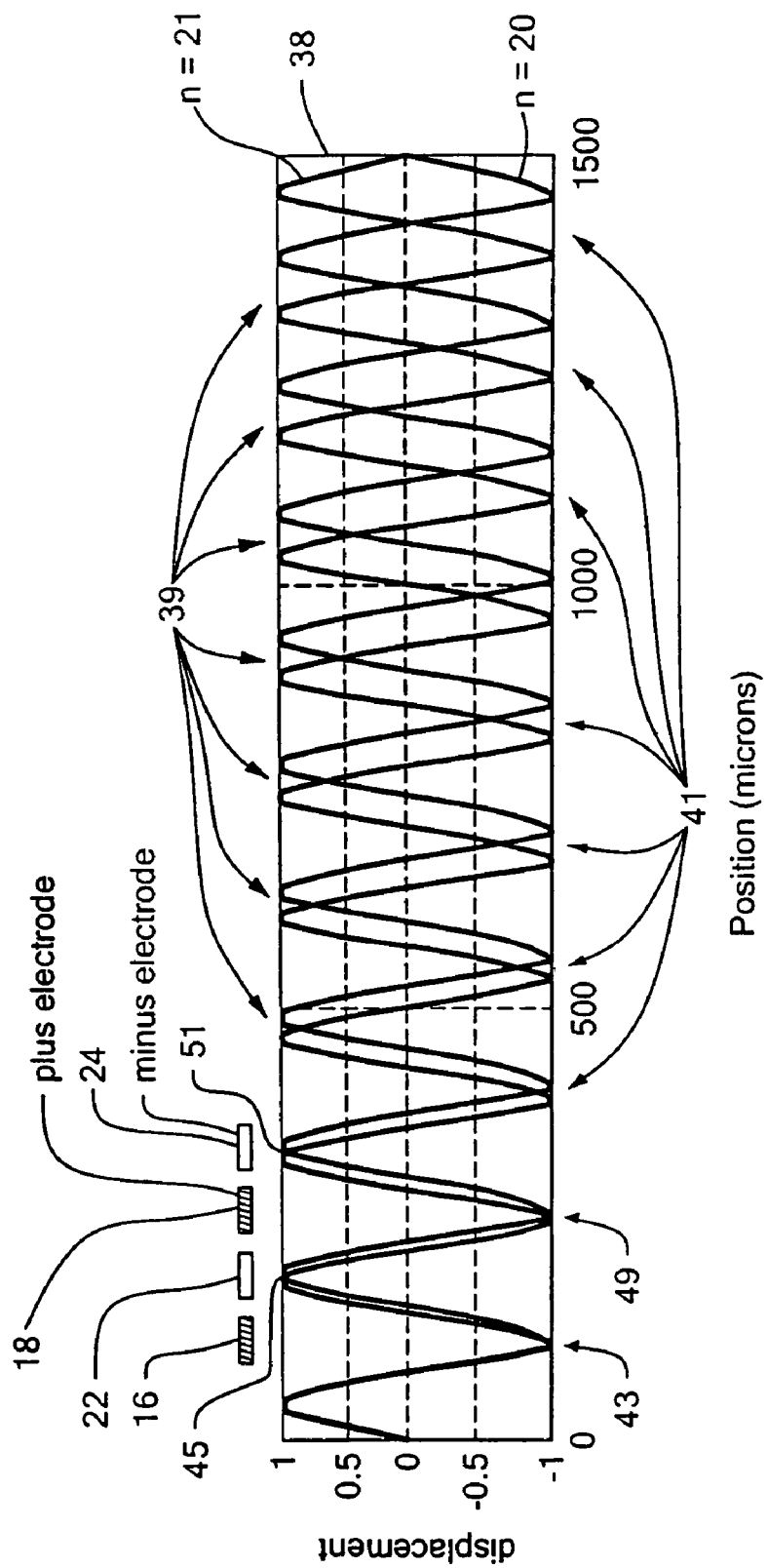
FIG. 2 is a graph showing the relationship of eigenmodes displacements to drive teeth for the sensor shown in FIG. 1.
Figure 3A:
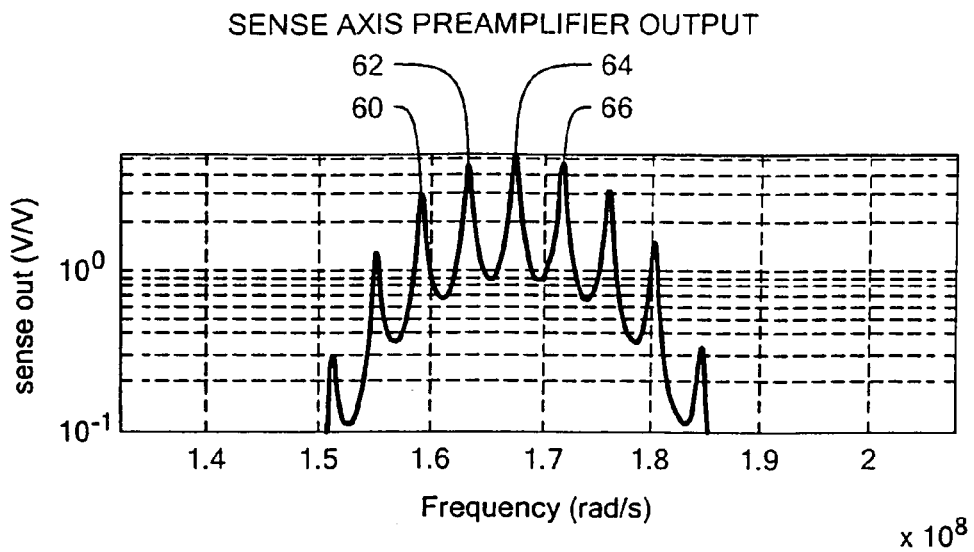
FIG. 3A is a graph showing the typical output for the wave sensor shown in FIG. 1.
Figure 3B:
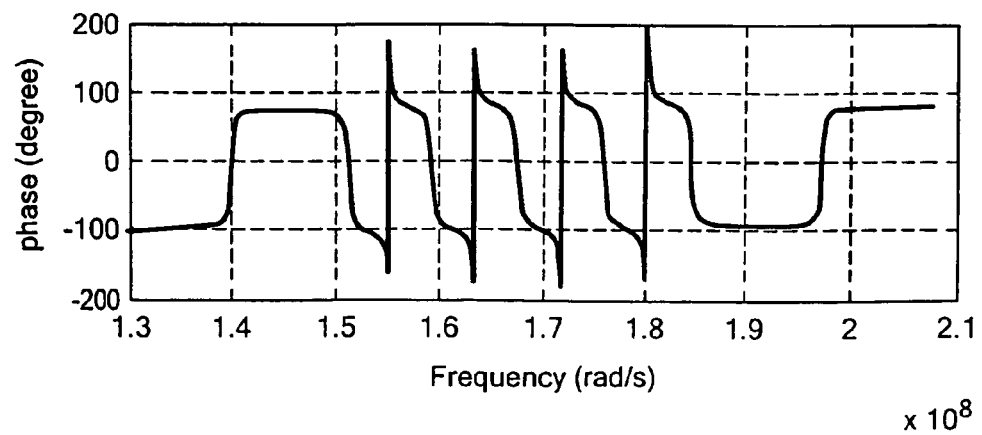
FIG. 3B is a graph showing the irregular phase response for the peaks shown in FIG. 3A.

For example, FIG. 2 shows the modal displacement for longitudinal eigenmodes, with n=20 and n=21, (where n=mode number≈½ sine periods) of flexural plate 38 shown in FIG. 1. As shown in FIG. 2, there is limited number of drive teeth 16, 18, 22, and 24 relative to the number of eigenmodes peaks 39 and 41. The result is that not only are the n=20 eigenmodes perfectly aligned with the drive teeth 16, 18, 22, and 24 excited, but other eigenmodes are also excited, as shown by arrows 43, 45, 49, and 51. The increased number of eigenmodes excited produces a series of resonance peaks of similar amplitude as shown by peaks 60, 62, 64 and 66, FIG. 3A, and irregular phase, as shown in FIG. 3B. The result is increased complexity in the electronic design and operation of prior art flexural plate wave sensor 10.

Prior art sensor 10, FIG. 1 also includes sense comb 26 and 32, typically at the opposite end of flexural plate 38 from drive combs 14 and 26, with sense teeth 28, 30, and 34, 36, respectively. As discussed above in the Background section, prior art sensor 10 relies on a theory based on surface acoustic waves (SAW) wherein waves propagate away from drive combs 14 and 20 toward sense combs 26 and 32, as indicated by arrow 50, FIG. 4, and back reflections are regarded as interference. Reliance on SAW theory, however, does not account for numerous small peaks produced by sensor 10, results in calculated gains which are low, and cannot account for sharp phase drops.

Figure 5:
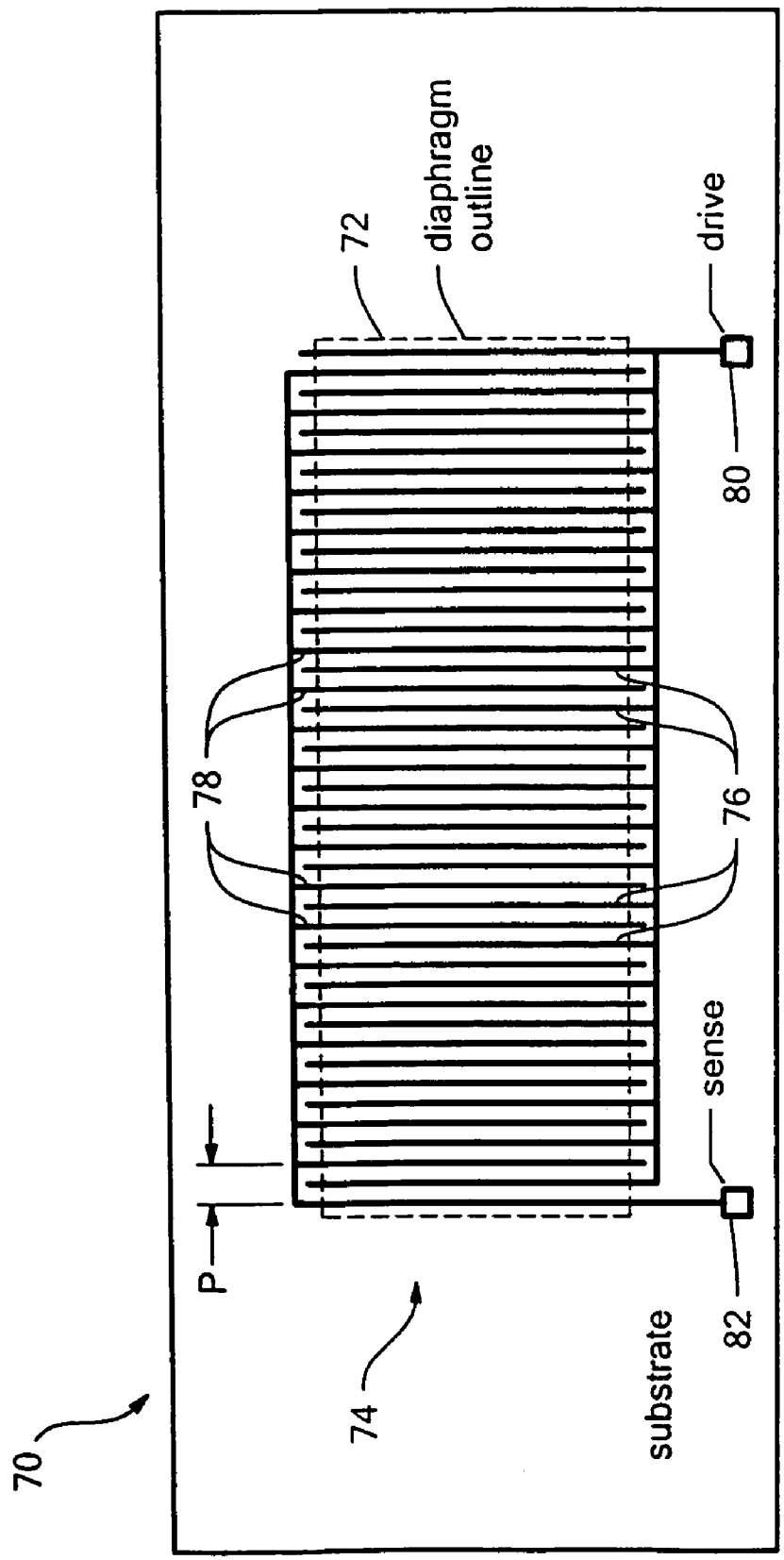
FIG. 5 is a schematic top view of one embodiment of the flexural plate wave sensor in accordance with the subject invention.

In contrast, flexural plate wave sensor 70, FIG. 5 of the subject invention includes flexural plate 72 having a length and a width, and comb pattern 74 over flexural plate 72 with drive teeth 76 disposed across the entire length of flexural plate 72 to reduce the number of eigenmodes excited in plate 72. In one design, comb pattern 74 is aligned with all the eigenmodes of flexural plate 72. In a preferred embodiment, only one eigenmode is excited. The result is that flexural plate wave sensor 70 outputs a single pronounced peak, e.g., peak 80, FIG. 6A, with a distinct phase, as shown in FIG. 6B, or a pronounced peak much larger than any of the other peaks, e.g., peak 82, FIG. 7A, compared to peaks 84, and 86, with a distinct phase, as indicated by arrow 89, FIG. 7B. This is in stark contrast to the peaks of similar amplitude and irregular phase produced by prior art sensors, as shown in FIGS. 3A and 3B. The result is a significant simplification in the operation and design of flexural plate wave sensor 70, FIG. 5. With only a single mode capable of being excited, the design of closed loop electronics of this invention, discussed below, improves stability of the system because erroneous readings do to interference created by mode hopping from other eigenmodes (as shown in FIGS. 3A and 3B) is not possible.

In one design in accordance with this invention, sensor 70 further includes sense teeth 78 disposed across the entire length of flexural plate 72. In one embodiment, sense teeth 78 and drive teeth 76 face in opposite directions. In this design, sense teeth 78 are interleaved with drive teeth 76. Sense teeth 78 are typically aligned with the eigenmodes excited in flexural plate 72 to detect the output produced by drive teeth 76.

In one example of this invention, comb pattern 74 is made of copper. In other examples, comb pattern 74 is made of titanium-platinum-gold (TiPtAu), titanium-platinum (TiPt), aluminum, or any known materials or combination of materials known to those skilled in the art. Typically, comb pattern 74 is approximately 0.1 μm thick and includes wire bond pad areas 80, and 82, FIG. 5.

Figure 8:
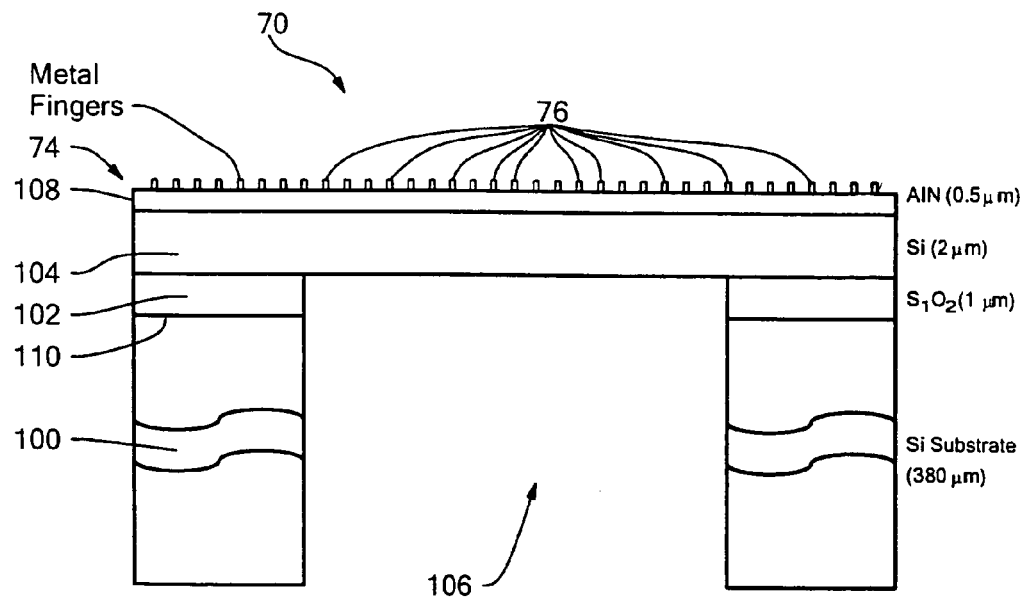
FIG. 8 is a schematic side view showing the various layers of the flexural plate wave sensor of this invention.

Flexural plate wave sensor 70 is typically comprised of several layers as shown in FIG. 8. Sensor 70 may include base substrate 100, typically a silicon substrate 380 μm thick and etch stop layer 102, ideally 1 μm thick and made of silicon-oxide ($SiO_2$) disposed over base substrate 100. Ideally, sensor 70 also includes membrane layer 104, typically made of silicon or similar material and is disposed over etch stop layer 102 and cavity 106. Additional silicon is typically grown to form membrane layer 104 (e.g., diaphragm layer). Cavity 106 has substantially parallel interior walls and is disposed within base substrate 100 and etch stop layer 102 thereby exposing a portion of membrane layer 104. In one example, piezoelectric layer 108 with a thickness of 0.5 μm is disposed on membrane layer 104. Comb pattern 74 with drive teeth 76 and sense teeth 78 (as also shown in FIG. 5) is disposed over piezoelectric layer 108. Typically, layer 104 is connected to ground (not shown). Piezoelectric layer 108 is ideally formed from a material such as aluminum nitride, zinc oxide, and lead zirconium titanate.

In other designs, base substrate 100 is a silicon-on-insulator (SOI wafer) and includes upper surface of silicon (e.g., membrane 104) bonded to etch stop layer 102. Ideally, grounding contacts to silicon layer (e.g., membrane 104) are provided by etching an opening into piezoelectric layer 108. In one preferred example, titanium-platinum-gold metal or titanium-platinum is patterned to define comb pattern 74, FIG. 5 with drive teeth 76 and sense teeth 78 disposed across the entire length of piezoelectric layer 108, FIG. 8. Ideally, comb pattern 74 further defines wire bond pad areas 80 and 82, FIG. 5 and grounding contacts (not shown). Typically, drive teeth 76 and sense teeth 78 are 300 μm to 2000 μm in length and the spacing between the drive and sense teeth is approximately 25 to 50 μm.

As shown above, the unique design of comb pattern 74 of flexural plate wave sensor 70 with drive teeth 76 disposed across the entire length of flexural plate 72 effectively reduces the number of eigenmodes excited in the flexural plate and outputs a single pronounced peak, or a peak much larger than any of the other peaks output by sensor 70. The result is a simplification in the operation and design of flexural wave plate sensor 70.

Figure 11A:
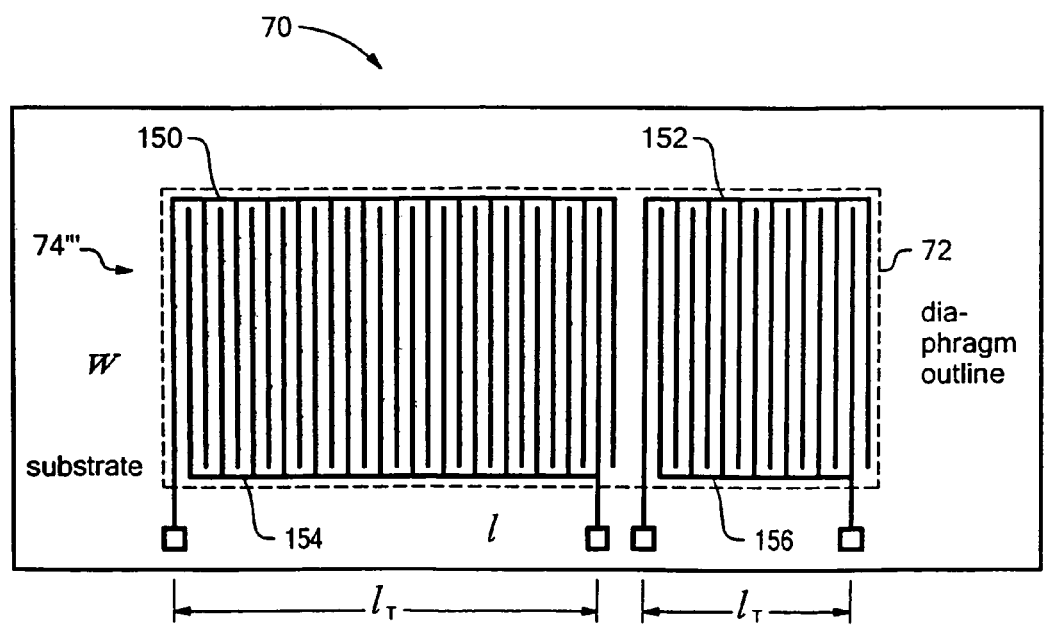
FIG. 11A is a schematic top view of another design of the comb pattern of the flexural plate wave sensor of this invention.
Figure 11B:
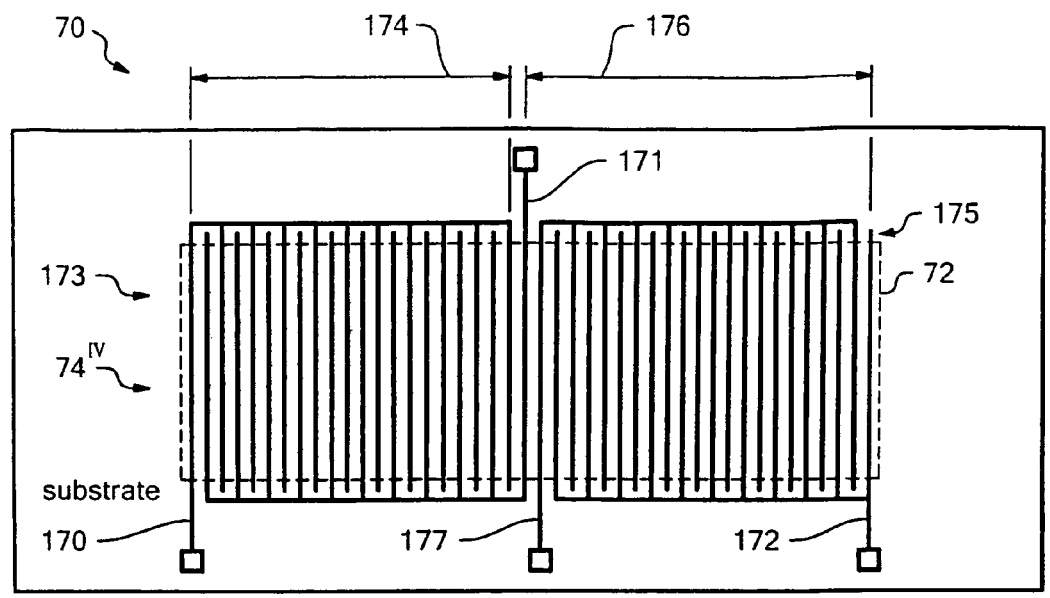
FIG. 11B is a schematic top view of another design of the comb pattern of the flexural plate wave sensor of this invention.
Figure 12:
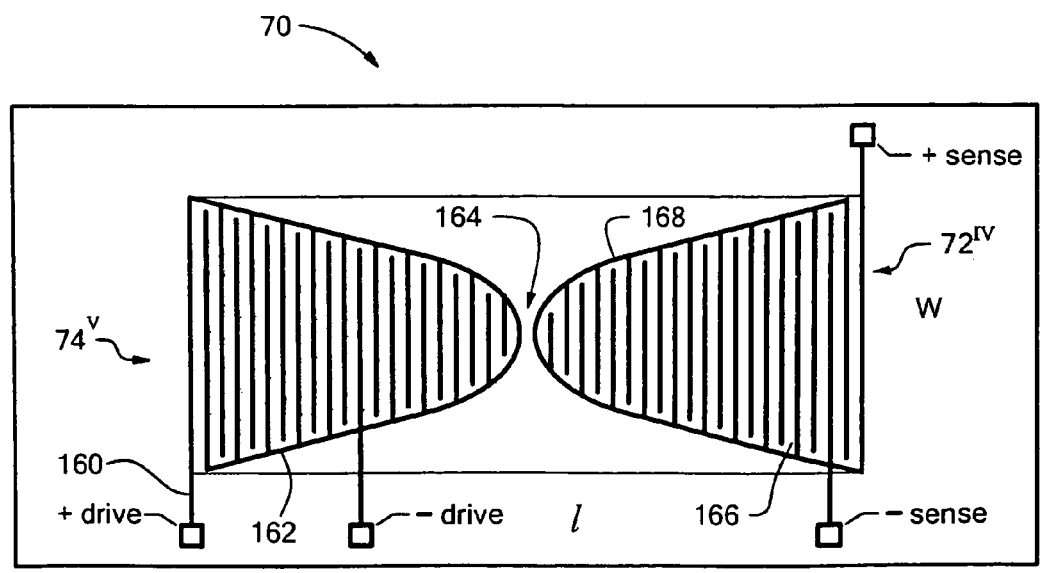
FIG. 12 is a schematic top view of yet another design of the comb pattern of the flexural plate wave sensor of this invention.

Unique comb pattern 74 may take several forms including sets of interleaved drive teeth and interleaved sense teeth which each span the entire length and approximately fifty percent of the width of the flexural plate (FIG. 9), two sets of interleaved drive and sense teeth wherein each set of interleaved drive and sense teeth spans the entire length and approximately fifty percent of the width of the flexural plate (FIG. 10), two sets of interleaved drive and sense teeth wherein one set of interleaved drive and sense teeth spans approximately seventy-five percent of the length of the flexural plate and the other set spans approximately twenty-five percent of the flexural plate (FIG. 11), and unique curved sets of drive and sense teeth (FIG. 12). Other equivalent embodiments may occur to those skilled in the art.

Figure 9:
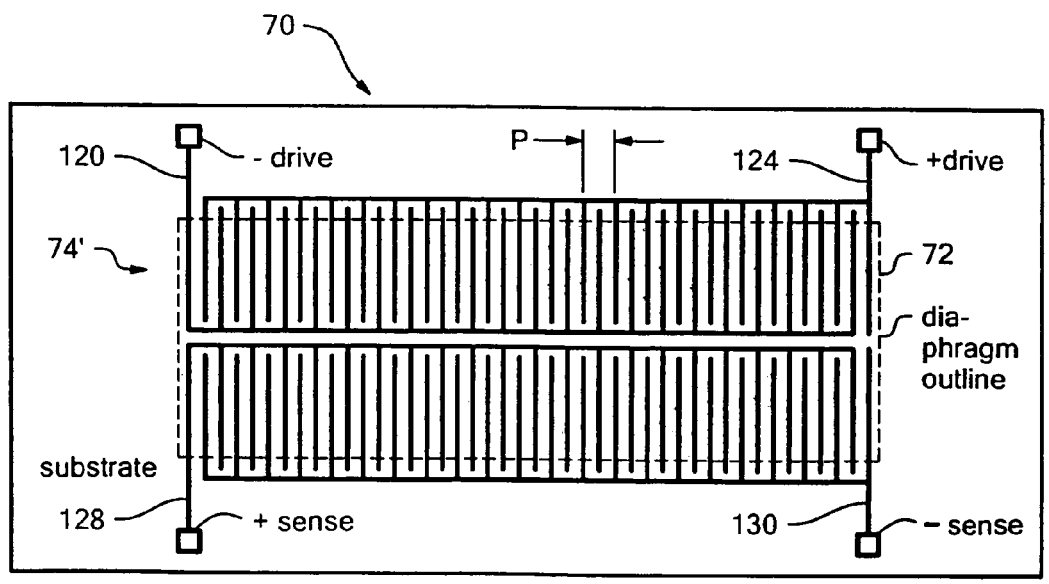
FIG. 9 is a schematic top view of another embodiment of the comb pattern of the flexural plate wave sensor of this invention.

Comb pattern 74', FIG. 9 includes first set 120 of drive teeth and second set 124 of drive teeth disposed across the entire length of flexural plate 72. Comb pattern 74' may also include first set 128 of sense teeth and second set 130 of sense teeth also disposed across the entire length of flexural plate 72 and are used to sense the output provided by first set 120 and second set 124 of drive teeth. In one example, first set 120 of drive teeth is driven at a negative polarity and second set 124 of drive teeth is driven at a positive polarity to align with the negative and positive peaks of the eigenmodes of flexural plate 72 and aid in the reduction of eigenmodes excited. Similarly, first set 128 of sense teeth is driven at a positive polarity and second set 130 of sense teeth is driven at a negative polarity. First set 120 and second set 124 of drive teeth may face in opposite directions and are interleaved with each other. Similarly, first set 128 and second set 130 of sense teeth face in opposite directions and are interleaved with each other. In this design, first set 120 of drive teeth is interleaved with second set 124 drive teeth which together are disposed across the entire length of flexural plate 72 and span approximately 50 percent of the width of flexural plate 72. Similarly, first set 128 of sense teeth is interleaved with second set 130 of sense teeth which together are disposed across the entire length of flexural plate 72 and span the remaining 50 percent of the width of flexural plate 72. The design of comb pattern 74' not only reduces the number of eigenmodes excited but also helps reduce the number of peaks output by sensor 70'.

Figure 10:
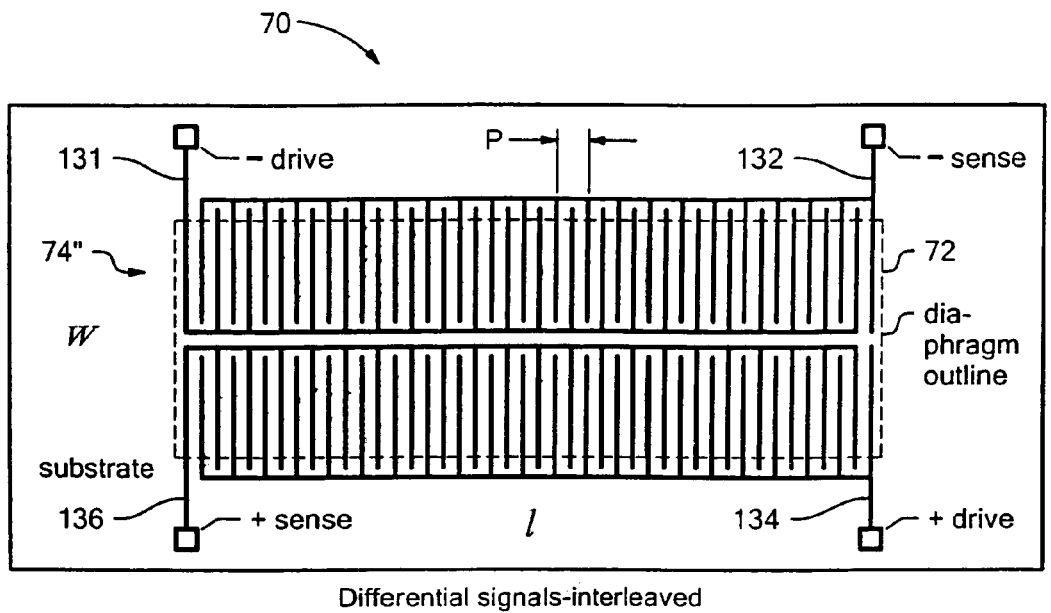
FIG. 10 is a schematic top view of another example of a comb pattern for the flexural plate wave sensor of this invention.

In another example of this invention, the design of comb pattern 74' described above is modified to interleave the first set of drive teeth with the first set of sense teeth as shown in FIG. 10. Comb pattern 74" includes first set of drive teeth 131 interleaved with first set of sense teeth 132. Interleaved sets 131 and 132 are disposed across the entire length of flexural plate 72 and fifty percent of the width of flexural plate 72. Comb pattern 74" also includes second set of drive teeth 134 interleaved with second set of sense teeth 136, which similarly span the entire length of flexural plate 72 and fifty percent of the width of flexural plate 72. Typically the sets of drive teeth (e.g., sets 131 and 134) and the sets of sense teeth (e.g., sets 132 and 136) are driven at opposite polarities. Similar to the above design in FIG. 9, this design not only reduces the number of eigenmodes excited but also reduces the number of peaks produced by sensor 70.

In yet another design, comb pattern 74''', FIG. 11A includes first set 150 of drive teeth and second set 152 of drive teeth. First set 150 spans approximately 75 percent of flexural plate 72 and second set 152 spans approximately 25 percent the length of flexural plate 72. Comb pattern 74''' may further include first set 154 of sense teeth which spans approximately 75 percent of the length of flexural plate 72 and is interleaved with first set 150 of drive teeth. Comb pattern 74''' may also include second set 154 of sense teeth which span approximately 25 percent of the length of flexural plate 72 and is interleaved with second set 152 of drive teeth. This design also reduces the number of eigenmodes excited in flexural plate 72.

In one embodiment, comb pattern 74$^{iv}$, FIG. 11B may include drive teeth 170 and sense teeth 172 disposed over flexural plate 72. Drive teeth 170 span approximately fifty percent of length of the flexural plate 72, as indicated by arrow 174, and sense teeth 172 span approximately fifty percent of the length of flexural plate 72, as indicated by arrow 176. Comb pattern 74$^{iv}$ similarly reduces the number of eigenmodes excited in flexure plate 72.

In another design, comb pattern 74$^{iv}$ may include set of drive teeth 173 which includes drive teeth 170 and drive teeth 171. Set of drive teeth set 173 spans approximately fifty percent of the length of flexural plate 72, similarly indicated by arrow 174. Comb pattern 74$^{iv}$ also includes set of sense teeth 175 which includes sense teeth 172 and sense teeth 177. Set of sense teeth set 175 spans approximately fifty percent of the length of flexural plate 72, as indicated by arrow 176. This design also reduces the number of eigenmodes excited in flexural plate 72. Although as shown in FIG. 11B, set of drive teeth 173 includes drive teeth 170 interleaved with drive teeth 171 and set of sense teeth 175 includes sense teeth 172 interleaved with sense teeth 177, this is not a necessary limitation of this invention, as drive teeth (e.g., drive teeth 170 or drive teeth 171) may also be interleaved with the sense teeth (e.g., sense teeth 172 or 177).

In another design in accordance with this invention, comb pattern 74$^{v}$, FIG. 12 includes first set 160 of drive teeth and second set 162 of drive teeth disposed across approximately 50 percent of the length of flexural plate 74. First set 160 and second set 162 of drive teeth span approximately the entire width of flexural plate 74 at one end and curve downward towards center 164 of flexural plate 74. The unique design of comb pattern 74$^{v}$ helps reduce the number of eigenmodes excited in the plate and also aids in reducing the number of peaks output by sensor 70. Comb pattern 74$^{v}$ may also include first set 166 of sense teeth interleaved with second set 168 of sense teeth of similar configuration to first and second sets 160, and 162 of drive teeth as described above.

Figure 13:
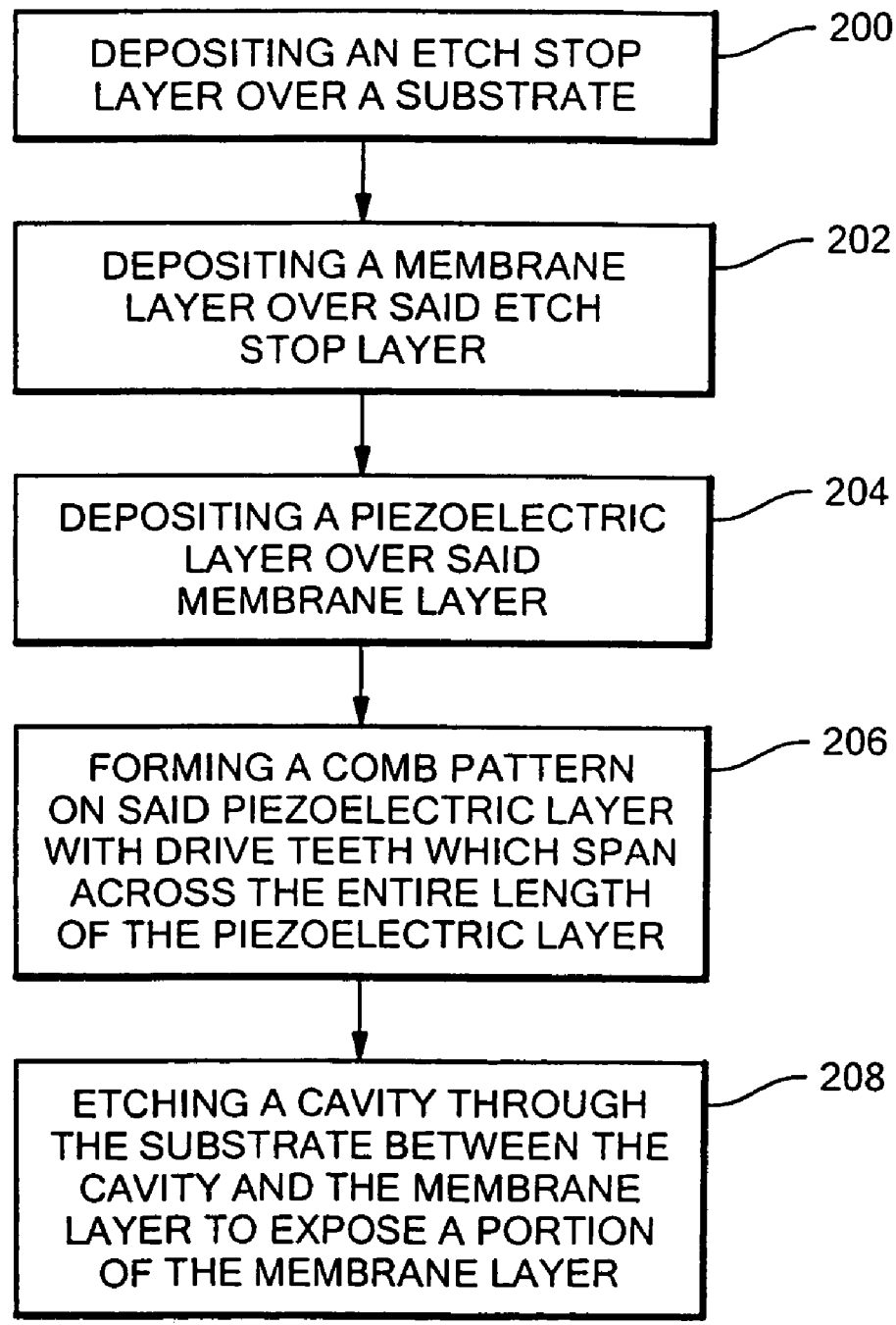
FIG. 13 is a flowchart showing the primary steps associated with one method of manufacturing a flexural plate wave sensor in accordance with this invention.

The method for manufacturing the flexural plate wave sensor 70 of this invention includes the steps of: depositing an etch top layer 102, FIG. 8 over substrate 100, step 200, FIG. 13; depositing (e.g., growing additional silicon) membrane layer 104, FIG. 8 over etch top layer 102, step 202, FIG. 13; depositing piezoelectric layer 108, FIG. 8 over membrane layer 104, step 204, FIG. 13; forming comb pattern 74, FIG. 8 (and FIGS. 5, and 9-11) on piezoelectric layer 108 with drive teeth 76 which span across the entire length, or portion thereof, of piezoelectric layer 108, step 206, FIG. 13; and etching cavity 106, FIG. 8 through substrate 100 between cavity 106 and membrane layer 104 to expose a portion of membrane layer 104, step 208, FIG. 13. In other examples, a silicon-on-insulator wafer (SOI) is employed which includes the oxide layer (e.g., etch stop layer 102) and the silicon diaphragm layer (e.g., membrane layer 104) already bonded together.

As shown above, the robust flexural plate wave sensor of the subject invention includes a comb pattern of several unique configurations which is disposed across the entire length of the flexural wave plate and reduces the number of eigenmodes excited in the plate thereby providing for a simple operation and design of the flexural wave plate. The unique comb pattern with drive teeth that span the entire length of the flexural wave plate provides the ability for the comb pattern to be aligned with the eigenmodes of the flexural wave plate. The result is the ability for flexural plate wave sensor 70 to produce a single pronounced peak, or a peak much larger than any of the other peaks, and provide greater stability, improved performance, and simplification of the design of the flexural plate wave sensor.

Figure 4:
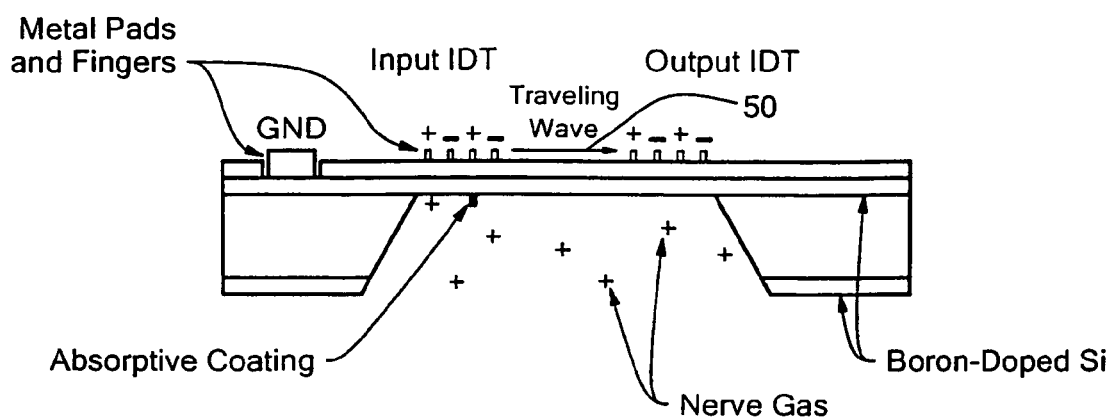
FIG. 4 is a schematic side view showing the direction of wave propagation of the sensor shown in FIG. 1.

As stated in the Background section above, prior art sensor 10, FIG. 1 utilizes drive combs 14 and 20 and sense combs 26 and 32 at opposite ends of the flexural plate. Prior art sensor 10 relies on theory based on an analogy to surface acoustic waves (SAW) wherein the waves propagate away from the drive combs 14 and 20 toward the sense combs 26 and 32, as shown in FIG. 4, and back reflections are regarded as interference.

The inventors hereof realized that such an analogy to SAW was incorrect for most flexural plate wave devices. In particular, design with simple edge conditions, such as the flexural plate shown in FIG. 14 and FIGS. 9-11, actually behaves as a resonating plate. The analysis below, equations (1) through (14), is based on modeling flexural plate 302, FIG. 14 as a thin beam. Comparisons to product performance and calculations of flexural plate 302 eigenfrequencies indicate that the beam model is valid for resonating plate 302 and sensor 300, as well as sensor 70 as shown in FIGS. 5 and 9-11. Equations (16) and (17) below augment the simple beam model to consider additional modes across the flexured plate 302 thickness.

Figure 14:
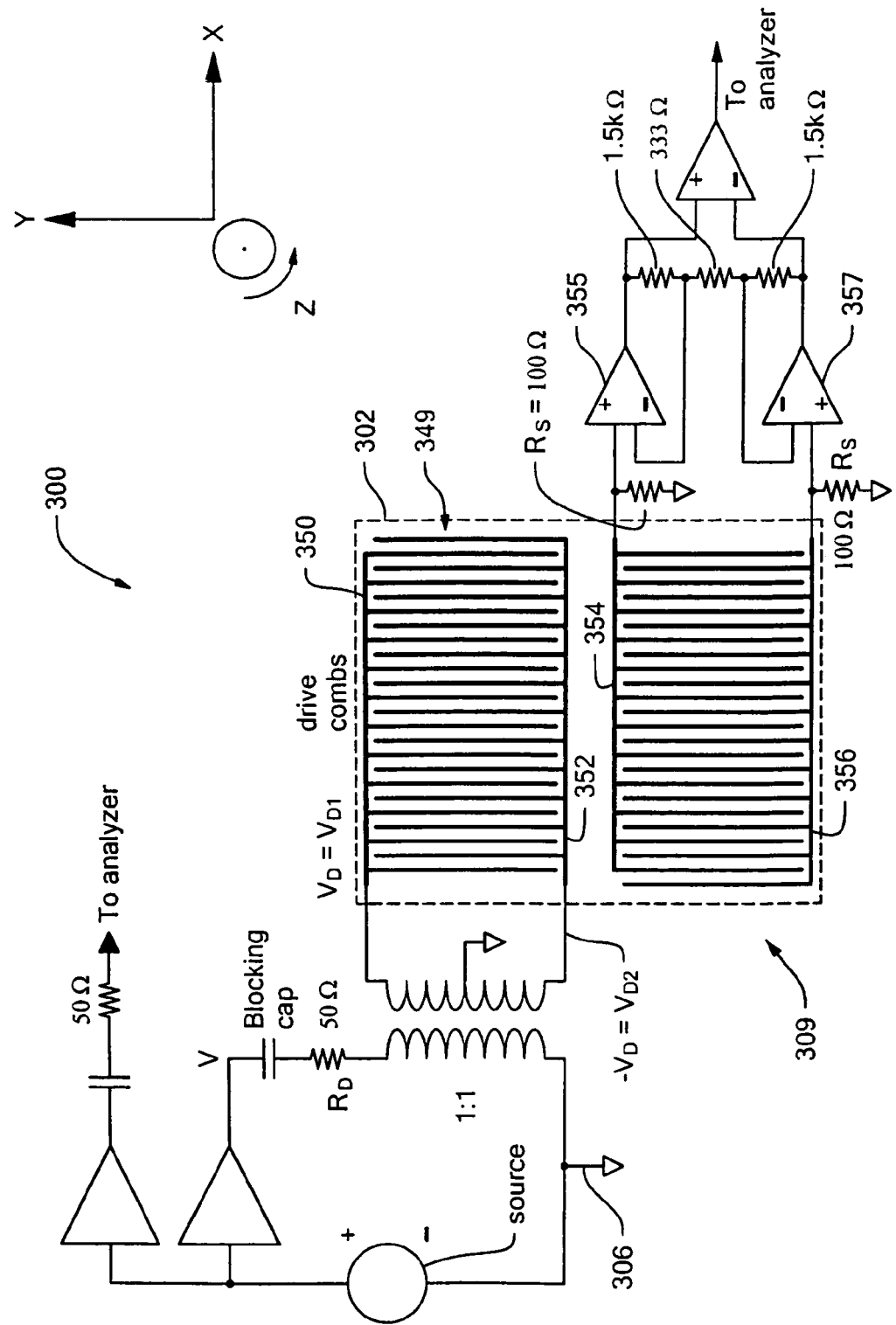
FIG. 14 is a schematic diagram of the circuitry associated with one embodiment of the flexural plate wave sensor in accordance with the subject invention.

As shown in FIG. 14, the drive voltage of flexural wave plate sensor 300, which includes flexural plate 302, is referenced to zero and applied to center grounded transformer 304 which applies $+V_D$ to one electrode and $-V_D$ to the other. The input side of the transformer 304 is connected to ground 306 and $V_D$. The output side is center tapped so that the ends are $+V_D$ and $-V_D$. In another example of this invention, one port operation may be employed using the drive circuit as an output, such as with a Pierce or series oscillator as known to those skilled in the art. A drive pair consists of two electrodes, e.g., electrodes or drive combs 350 and 352 at $+V_D$ and $-V_D$. A sense pair may consist of two electrodes or sense combs, e.g., electrodes or sense combs 354 and 356, which are typically connected to the inputs of differential amplifiers, such as differential amplifiers 355 and 357, respectively. In one design, all the electrodes, e.g., electrodes or combs 350, 352, 354 and 356 are deposited on top of the piezoelectric layer (not shown) of flexural plate 302. (Similar to the design of flexural plate 70, FIG. 8 discussed above.) Silicone layer 309, FIG. 14 is typically connected to ground 306.

The relationship between the eigenmodes and flexural plate voltage is shown below. The derivation of equation (1) below is disclosed in "Modeling Flexural Plate Wave Devices", Weinberg et al., Journal of Microelectro Mechanical Systems, Vol. 9, (September 2000), incorporated herein by reference. The following equations are based on a thin beam vibrating in the z direction as shown in FIG. 14. The displacement at any position is given by:

$$z(t) = \sum_{n=1}^{\infty} A_n(t)\varphi_n(x) \tag{1}$$

The equation of motion for each mechanical mode is:

$$m_p \ddot{A}_n + b\dot{A}_n + m\omega_n^2 A_n = \frac{\int_0^\ell \varphi_m(x) f(x,t) dx}{\int_0^\ell \varphi_n^2(x) dx} = f_n(t) \quad (2)$$

where $$\phi_n(x) \approx \sin\left(\lambda_n x - \frac{\pi}{4}\right) =$$

eigenmode shape for built-in diaphragm edges, which equals $\sin(\lambda_n x)$ for simple supports, $$\lambda_n = \frac{2n+1}{2L}\pi$$

equals eigenvalue for built-in edges, and $\lambda_n = n\pi$ is the eigenvalue for simply supported edges. Further, where n is a positive integer equal to the number of half wavelengths in length L, $m_p$ is the mass per unit length, b is the damping per unit length, $A_n$ is the amplitude of motion of the excited n'th mode, L is flexural plate length, and $f_n(t)$ is the forcing function for mode n.

For simple and built-in supports, the angular resonant frequency is related to the wave number $\lambda$ by:

$$\omega_n = \sqrt{\frac{D}{m}} \lambda_n^2 \quad (3)$$

where D is the rigidity.

Assuming the mode shape is given by:

$$\varphi_n(x) = \sin\left(\frac{n\pi x}{\ell} - \varphi\right) \quad (4)$$

Also assume pinned beams for which $\phi=0$. Because of the large number of modes, pinned and built-in beams differ little. Assume also that the beam is driven by a force density whose first harmonic is:

$$w(x,t) = w_a \sin\left(\frac{2\pi x}{P} - \theta\right) \sin(\omega t) \quad (5)$$

where $$w_a = -\frac{2\sqrt{2}}{\pi}\left(\frac{m\pi}{\ell_t}\right)^2 M_p V_D, M_p$$

is the magnitude of piezoelectric torque per volt applied to electrodes, $V_D$ is the voltage applied to drive teeth 352, $\theta$ is the alignment between comb fingers and reference, $l_t$ is length of transducer which equals mP/2, P is the comb pitch, and m is number of combs in transducer or the number of half sines in $L_t$.

With equations (2), (4) and (5), the modal forcing function is determined from:

$$f_n(t) = w_a \sin(\omega t) \frac{2}{\ell} \int_{x_o}^{x_o+\ell_t} \sin\left(\frac{n\pi x}{\ell} - \varphi\right) \sin\left(\frac{m\pi x}{\ell_t} - \theta\right) dx \quad (6)$$

where the comb starts at $x_o$ and ends at $x_o+l_t$. From equation (6) $\gamma_n$ is defined and relates the modal force to the input voltage:

$$\frac{f_n}{V_D} = k_n \gamma_n = \quad (7)$$

$$-\frac{2\sqrt{2}}{\pi}\left(\frac{m\pi}{\ell_t}\right)^2 M_p \sin(\omega t) \frac{2}{\ell} \int_{x_o}^{x_o+\ell_t} \sin\left(\frac{n\pi x}{\ell} - \varphi\right) \sin\left(\frac{m\pi x}{\ell_t} - \theta\right) dx$$

Equation (7) applies to both the comb and sense electrodes, e.g., comb pattern 350 with drive teeth 350 and 352, and sense teeth 354 and 356 (or any of the designs shown in FIGS. 5 and 9-12). The integral is taken over the transducer length $l_t$ as shown in FIG. 11, since the combs exert the force. With simple support, $\phi$ is equal to 0. The units of $\gamma$ are m/V and $\gamma$ is proportional to $1/\lambda_n^4$. When the combs and modes are aligned, $\theta$ is equal to 0 and the forcing function is:

$$f_n(t) = w_a \sin(\omega t) \frac{l_t}{l} \left\{ \frac{\sin\left[\left(\frac{l_t n}{l} - m\right)\pi\right]}{\left(\frac{l_t n}{l} - m\right)\pi} - \frac{\sin\left[\left(\frac{l_t n}{l} + m\right)\pi\right]}{\left(\frac{l_t n}{l} + m\right)\pi} \right\} \quad (8)$$

Figure 15A:
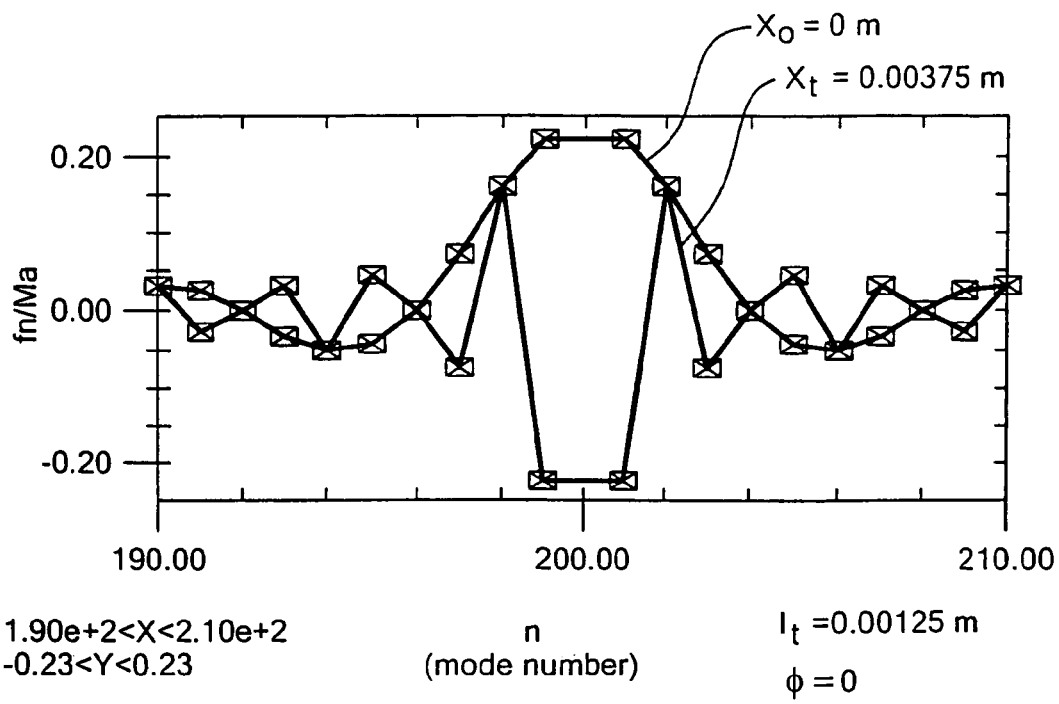
FIGS. 15A-15C are graphs showing several examples of the output of the flexural plate wave sensor of the subject invention.
Figure 15B:
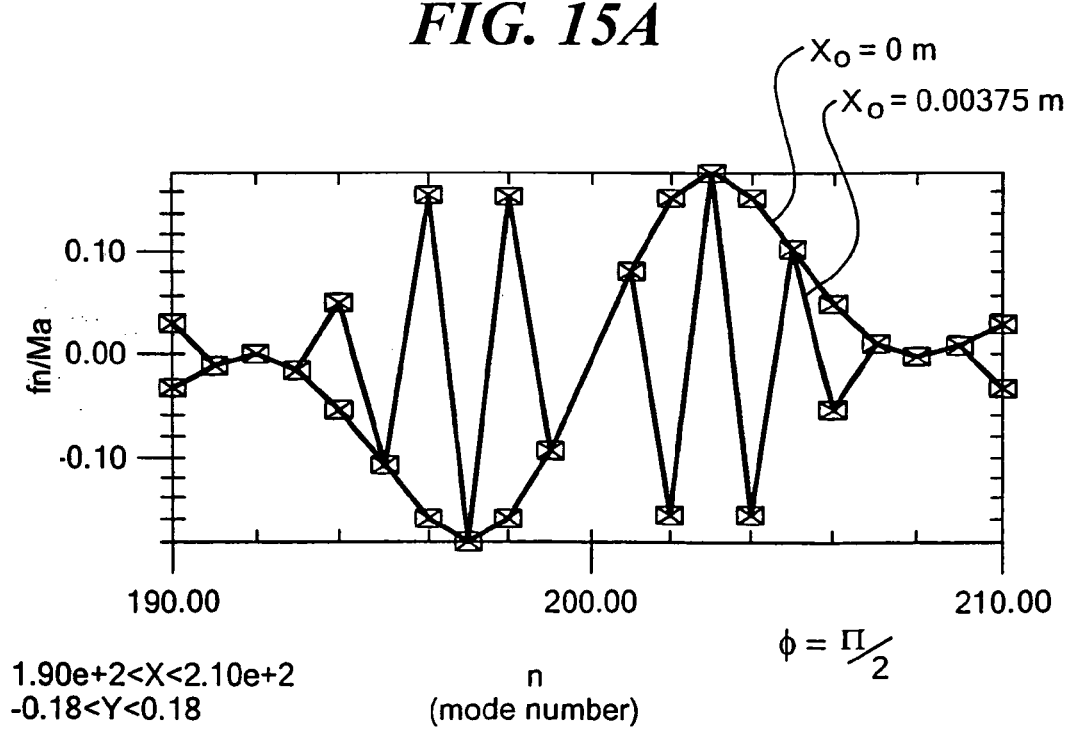
Figure 15C:
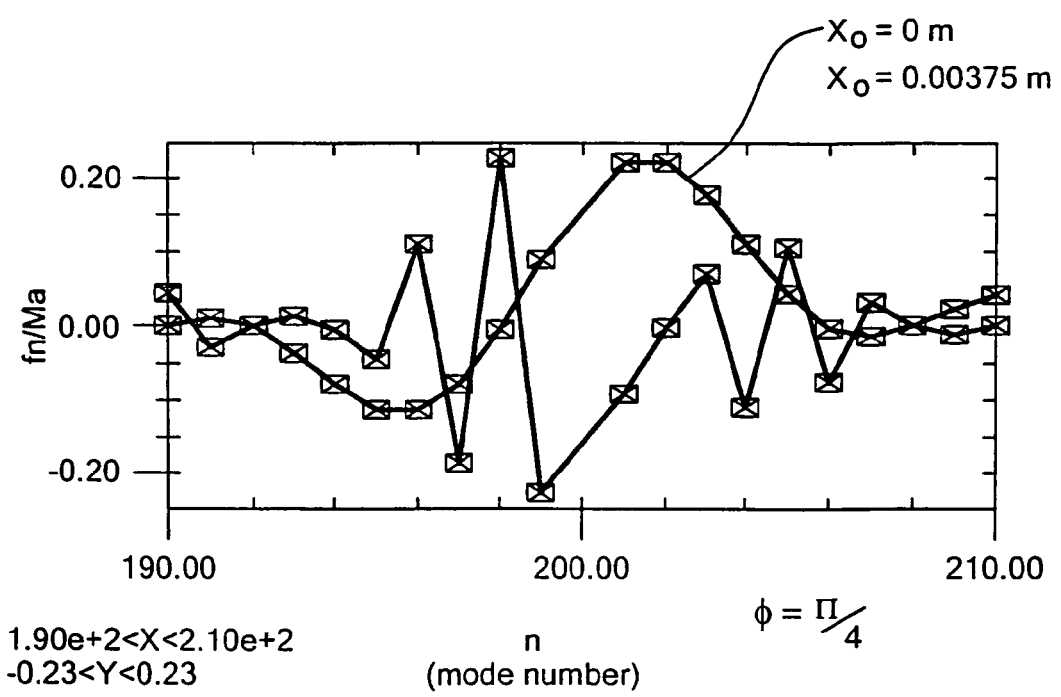

The model amplitudes responses $f_n(t)/[W_a \sin(\omega t)]$ for phase $\theta$ of zero, $\pi/4$, and $\pi/2$ are shown in FIGS. 15A-15C with a transducer length of 0.00125 meters, flexural plate 302, FIG. 14 a length of 0.005 meters, and m equals 50, yielding a 50 μm pitch. When the wavelength of the eigenmode matches the comb pitch, the maximum forcing of flexural plate wave sensor 300 is achieved.

Figure 6A:
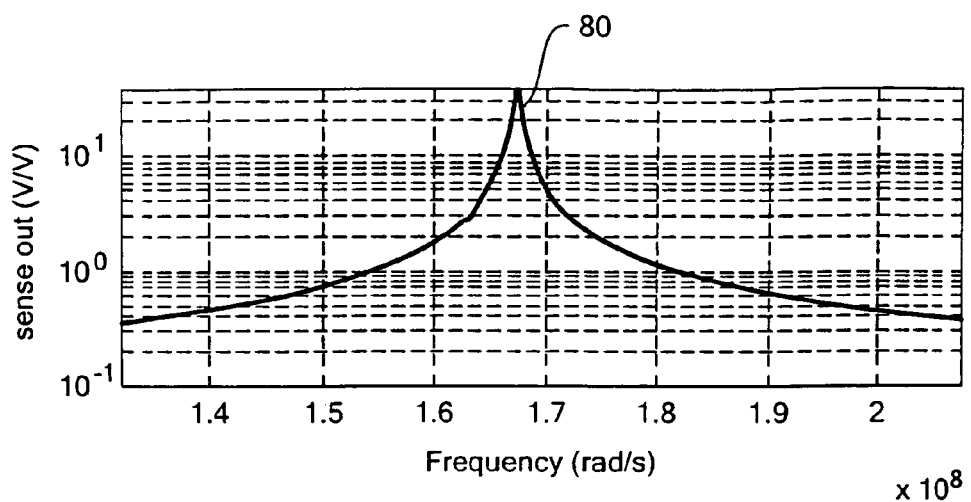
FIG. 6A is a graph showing a single pronounced peak output by the flexural plate wave sensor shown in FIG. 5.
Figure 6B:
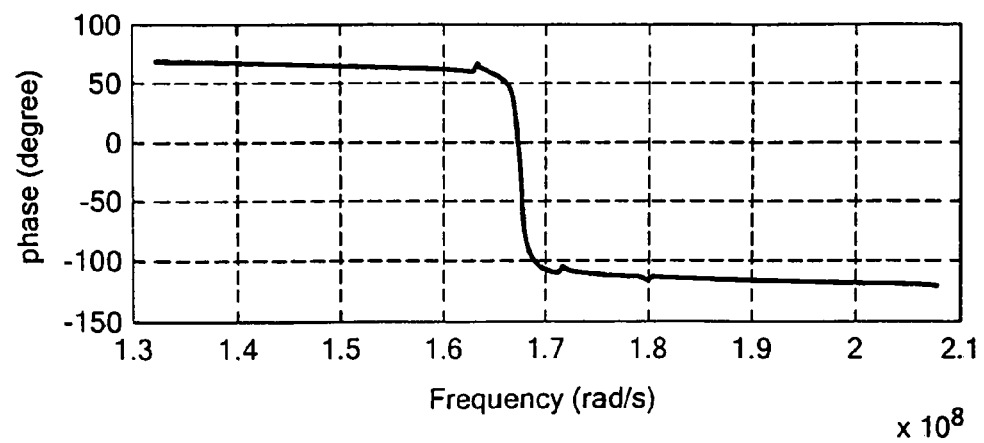
FIG. 6B is a graph showing a distinct phase response for the peak shown in FIG. 6A.
Figure 7A:
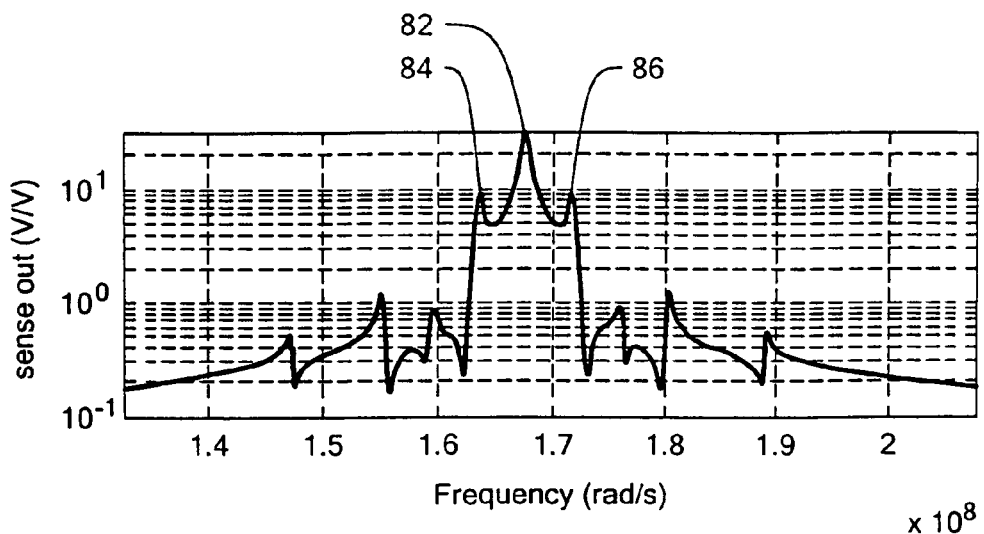
FIG. 7A is another graph showing several pronounced peaks of various magnitude output by the flexural plate wave sensor shown in FIG. 5.

In accordance with this invention, when the drive length, e.g., the length of comb pattern 300 with drive teeth 352 (or the designs shown in FIGS. 5 and 9-11) disposed across the entire length of flexural plate 302, only one mode in the x direction is excited and the response becomes a simple second order system, producing a single pronounced peak, as shown in FIG. 6A. Moreover, by varying the comb length and tooth width it is possible to trim the piezoelectric bending as a function of y which can force harmonics so that the y direction sinusoid harmonics are not excited.

In equation (8), the force per length w(x,t) was represented by its first harmonic. The modal forcing function $f_n(t)$ in equation (6) is dominated by terms with denominators which include $$\left(\frac{l_t n}{l} - m\right);$$

thus, higher harmonics of w(x,t) have larger values of m and contribute little to equation (8).

Coupling of beam modes into output utilizes the conversion of strain into charge on the flexural plate 302, FIG. 14. Assuming flexural plate 302 is grounded, the surface charge per unit length is described by:

$$Q_x = d_{31} Y b \epsilon_p (1 + v_P) \quad (9)$$

where $d_{31}$ is the piezoelectric constant relating z electric field to x strain, Y is Young's modulus of the piezoelectric material, $v_p$ is Poisson's ratio and b is the width of diaphragm.

Using equations (1) and (4), the peak x strain at area center for piezoelectric material, $\epsilon_p$, is related to the modal amplitudes by:

$$\epsilon_p = \frac{\Delta z_m}{R} = \frac{\partial^2 z}{\partial x^2} \Delta z_m = -\sum \left(\frac{n\pi}{l}\right)^2 \Delta y_m A_n(t) \sin\left(\frac{n\pi x}{l} - \varphi\right) \quad (10)$$

where $\Delta Z_m$ is the distance between the piezoelectric material's center of area and the flexural plate's neutral axis for torque inputs, and R=radius of curvature at position.

The total charge is calculated by integrating equation (9) over the electrodes (e.g., comb patterns 350 and 352, FIG. 14). Because of the sine function in equation (10), this integration is similar to a Fourier transform so that is easier to consider the first harmonics of the plate distribution:

$$Q = \int_{electrodes} Q_x dx \approx \frac{2\sqrt{2}}{\pi} \int_{x_o}^{x_o+l_t} Q_x \sin\left(\frac{m\pi x}{l_t} - \theta\right) dx \quad (11)$$

With equations (9) and (10) inserted into equation (11), the total charge on the sense or drive electrodes (e.g., drive teeth 350 and 352 or sense teeth 354 and 356) is:

$$Q = \sum_n \alpha_n A_n \quad (12)$$

where the coupling between modal amplitude and charge is given by:

$$\alpha_n = -\left(\frac{n\pi}{l}\right)^2 d_{31} Y b \Delta z_m \frac{l\sqrt{2}}{\pi} \left[\frac{2}{l} \int_{x_o}^{x_o+l_t} \sin\left(\frac{n\pi x}{l} - \varphi\right) \sin\left(\frac{m\pi x}{l_t} - \theta\right) dx\right] \quad (13)$$

The integral in brackets is identical to that used to calculate the modal force of equation (7). The units of $\alpha_n$ are Coul/m and $\alpha_n$ is proportional to $\lambda_n^2$.

Insert the piezoelectric diaphragm model into a lumped parameter model with other electrical circuit elements as follows. The piezoelectric comb pair, for example 349, typically includes two electrodes, e.g., 350 and 352, and ground plane 306. For a single mode, the static equation relating modal displacement and charge to electrode voltage and modal force is:

$$\begin{bmatrix} 1 & 0 & -\frac{\alpha_n}{2} \\ 0 & 1 & \frac{\alpha_n}{2} \\ 0 & 0 & 1 \end{bmatrix} \begin{bmatrix} Q_{D1} \\ Q_{D2} \\ A_n \end{bmatrix} = \begin{bmatrix} C+C_{12} & -C_{12} & 0 \\ -C_{12} & C+C_{12} & 0 \\ \frac{\gamma_n}{2} & -\frac{\gamma_n}{2} & \frac{1}{k_n} \end{bmatrix} \begin{bmatrix} V_{D1} \\ V_{D2} \\ f_n \end{bmatrix} \quad (14)$$

where C is capacitance from one plate to ground, $C_{12}$ is capacitance between positive and negative electrodes, $\alpha_n$, $\gamma_n$ are piezoelectric coupling coefficients defined in equations (7) and (13), $k_n$=modal stiffness, $D_1$ refers to a positive drive electrode, e.g., drive teeth 350, and $D_2$ refers to a negative drive electrode 352. The negative signs on $\alpha_n$ and $\gamma_n$ indicate that the negative electrodes are displaced 180 degrees from the positive electrodes. The voltage applied to the negative comb is minus that applied to the plus electrodes:

$$V_D = V_{D1} = -V_{D2} \quad (15)$$

With small coupling assumption implicit in equation (14), the voltages and currents applied to flexural plate plates are still described by equations (9) through (13). Equation (14) formulation results in $Q_{D2} = -Q_{D1}$ which is consistent with the circuit diagram of FIG. 14. $Q_{D1}$ is the integral of the current $I_2$ defined above. Symmetry and differential read out define:

$$Q = Q_{D1} - Q_{D2} \quad (16)$$

Equation (16) is simplified to:

$$\begin{bmatrix} 1 & -\alpha_n \\ 0 & 1 \end{bmatrix} \begin{bmatrix} Q \\ A_n \end{bmatrix} = \begin{bmatrix} 2(C+2C_{12}) & 0 \\ \gamma_n & \frac{1}{k_n} \end{bmatrix} \begin{bmatrix} V_D \\ f_n \end{bmatrix} \quad (17)$$

When adding the circuit resistors, the Q consists of two currents as outlined in equation (16). Equations (16) and (17) describe both the drive and sense electrode pairs.

The charge is the total charge summed over the electrode while the force is the modal force which is a force per unit length along the beam. When the mode period matches the combs' period:

$$\lambda_n = \frac{n\pi}{l} = \frac{m\pi}{l_t} \quad (18)$$

and the combs are aligned with the eigenmode [θ equals φ in equation 7], the piezoelectric equation (17) obeys a form of reciprocity as shown by:

$$\gamma_n k_n = \frac{2\alpha_n}{l} \quad (19)$$

The reciprocity demonstrates a symmetry between voltage, modal force, charge per length, and modal amplitude. When the eigenmodes are not aligned with the combs, equation (19) does not govern.

The results of the above are combined into a comprehensive dynamic flexural plate wave sensor of this invention which relates excitation voltage to the preamplifier output. For clarity, only 3 modes are included in this example. However, this is not a necessary limitation of this invention, as any number of modes may be included by those skilled in the art and shown in FIGS. 3A, 3B, 6A, 6B, 7A and 7B. As stated above, the charge includes both the plus and minus plates. The voltage and force applied directly to the piezoelectric material are shown as:

$$\begin{bmatrix} 1 & 0 & -\alpha_{D1} & -\alpha_{D2} & -\alpha_{D3} \\ 0 & 1 & -\alpha_{S1} & -\alpha_{S2} & -\alpha_{S3} \\ 0 & 0 & k_1 & 0 & 0 \\ 0 & 0 & 0 & k_2 & 0 \\ 0 & 0 & 0 & 0 & k_3 \end{bmatrix} \quad (20)$$

$$\begin{bmatrix} Q_D \\ Q_S \\ A_1 \\ A_2 \\ A_3 \end{bmatrix} = \begin{bmatrix} C_D & 0 & 0 & 0 & 0 \\ 0 & C_S & 0 & 0 & 0 \\ k_1\gamma_{D1} & k_1\gamma_{S1} & 1 & 0 & 0 \\ k_2\gamma_{D2} & k_2\gamma_{S2} & 0 & 1 & 0 \\ k_3\gamma_{D3} & k_3\gamma_{S3} & 0 & 0 & 1 \end{bmatrix} \begin{bmatrix} V_D \\ V_S \\ f_1 \\ f_2 \\ f_3 \end{bmatrix}$$

The force applied to the piezoelectric material is described by.

$$f_n = -b_n \dot{A}_n - m_p \ddot{A}_n \quad (21)$$

The voltage applied to the drive comb 350, FIG. 14 is:

$$V_D = V - sQ_D R_D \quad (22)$$

where V=voltage applied by the source and $R_D$ is the input resistor.

Assuming that the output preamplifier is at virtual ground, the sense voltage is given by:

$$V_s = -sQ_s \frac{R_s}{2} \quad (23)$$

where $R_S$ is the sense resistor. The factor of two accounts for the definition of Q of equation (15) which includes both the positive and negative electrodes. The MATLAB®code for equations (20) through (23) to obtain frequency responses is shown in FIGS. 16A-16C.

As a first approximation for a rectangular plate, e.g., flexural plate 302, FIG. 14 the eigenmodes in the x and γ directions are close to those derived from beam theory as shown by J. Blevins, *Formulas for Natural Frequency and Mode Shape*, Robert E. Krieger Publishing Co., Malabar, Fla. (1979). The displacement is a sinusoid in x multiplied by a sinusoid in y. For an isotropic or orthotropic rectangular plate built-in or simply supported on four edges, the eigenfrequencies (in Hz) are given approximately by:

$$f_{nm} = \frac{\pi}{2} \sqrt{\frac{G(n)^4}{l^4} + \frac{G(m)^4}{b^4} + \frac{2J(n)J(m)}{l^2 b^2}} \sqrt{\frac{Yh^3}{12m_a(1-v^2)}} \quad (24)$$

where n is the mode number along length, m is the mode number across width, l=length of plate, in one example 0.005 m, b is the width of plate, such as 0.001 m, G(n) equals n for simple supports and n+½ for all edges built-in, J(n)=n² for simple support and is equal to $$\left(n + \frac{1}{2}\right)^2 \left[1 - \frac{2}{\pi\left(n + \frac{1}{2}\right)}\right]$$

with all edges built-in, Y is Young's modulus, h is the plate thickness and $m_a$=mass per unit area.

For a simply supported plate, equation (24) becomes:

$$f_{nm} = \frac{\pi}{2} \sqrt{\frac{Yh^3}{12m_a(1-v^2)}} \left(\frac{n^2}{l^2} + \frac{m^2}{b^2}\right) \quad (25)$$

Figure 7B:
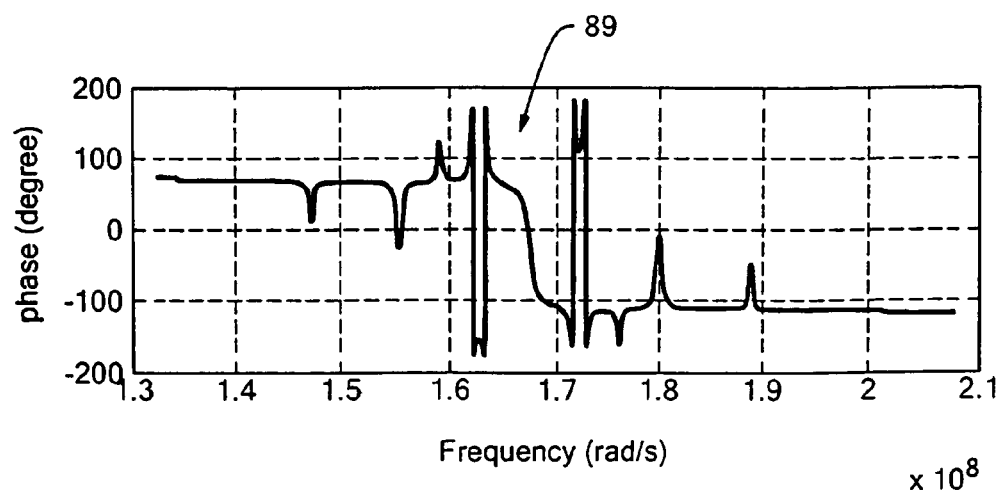
FIG. 7B is a graph showing a distinct phase response for the peaks shown in FIG. 7A.
Figure 17:
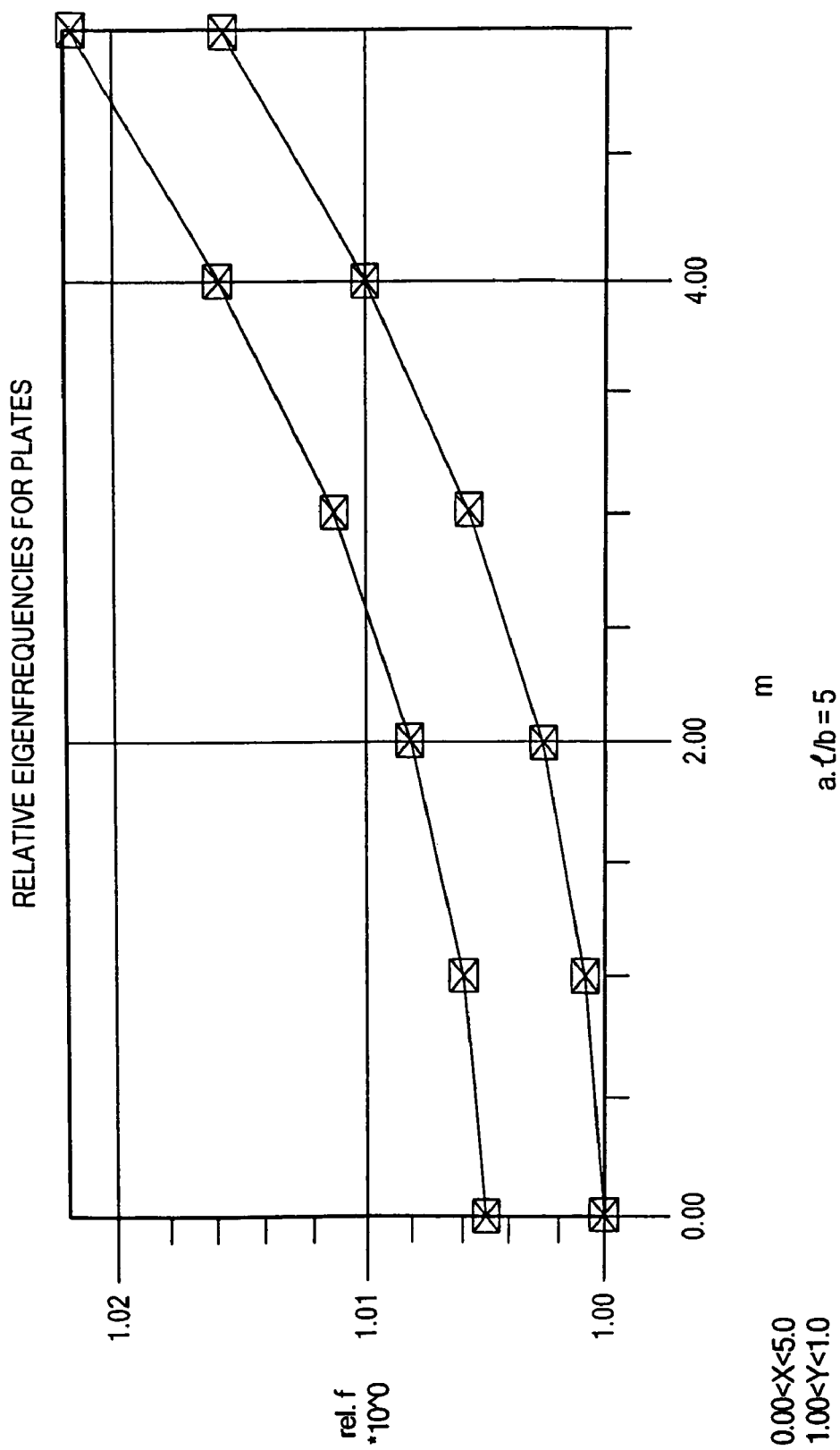
FIG. 17 is a graph showing the relative eigenfrequencies of one embodiment of the flexural plate wave sensor of this invention.
Figure 18:
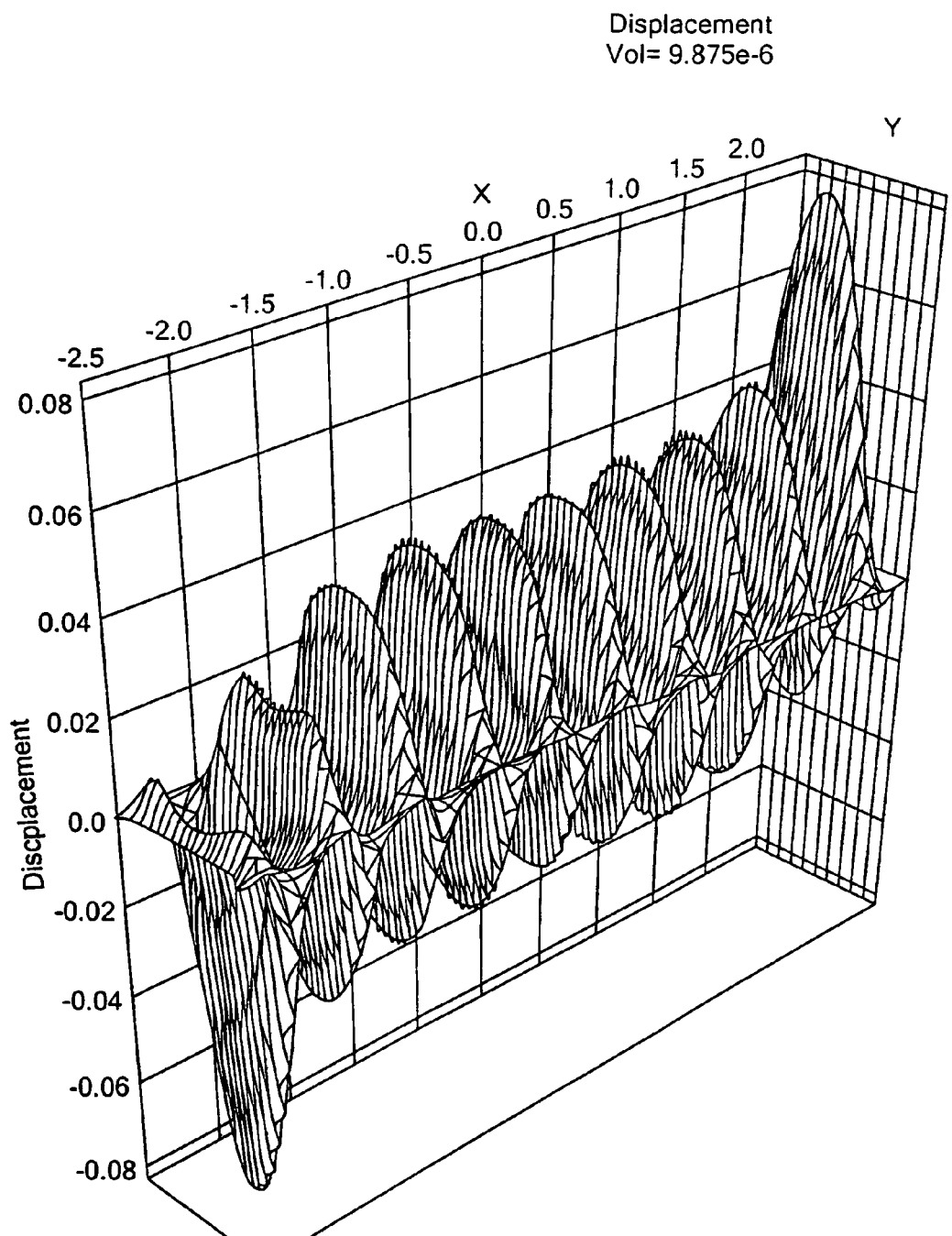
FIG. 18 is a graph showing the static plate deflections for a sinusoidal load on the flexural plate wave sensor of this invention.

For the nominal case, the eigenfrequencies relative to m=0 and simple support are plotted versus m in FIG. 17. For l/b=5. Equations (24) and (25) duplicates beam theory when m=0. The built-in eigenfrequency is 0.50% higher than the simple support. With m=1 and n=200, the built-in's resonant frequency is 0.085% larger than the m=0 simple beam case. This m=1 frequency is near the beam theory value and is the basic operating frequency. As shown in FIG. 18, displacements are close to the m=1 mode shape. Higher m modes are more half sines in the y (short) direction. With m=2, the next resonance is 0.21% above the basic operating frequency (m=1). With straight teeth, the excitation is an odd harmonic and should not be excited (except for fabrication deviations). For built-ins, the m=3 resonance is 0.6% higher than the fundamental. Although the excitation is square in the y direction, the response along a fixed x is largely sinusoidal as shown in FIG. 18. With square drive the third harmonic of the drive is ⅓ the fundamental. FIG. 3A shows a raggedness associated with prior art sensor 10 which crosses modes. In sharp contrast, flexural wave plate sensor 70, FIGS. 5, 9-11 and sensor 300, FIG. 14 in accordance with this invention, include the unique comb pattern which extends across the entire length of the flexural plate that produces simple pronounced peaks or peaks much larger than any other peaks as shown in FIGS. 6A and 6B with a distinct phase as shown in FIGS. 7A and 7B.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. A method for manufacturing a flexural plate wave sensor, the method comprising the steps of:
    depositing an etch-stop layer over a substrate;
    depositing a membrane layer over said etch stop layer;
    depositing a piezoelectric layer over said membrane layer;
    forming a comb pattern with drive teeth which span across an entire length of the piezoelectric layer on said piezoelectric layer, the comb pattern aligned with a number of eigenmodes of the flexural plate to reduce the number of eigenmodes excited in the plate and simplify the operation and design of the flexure plate wave sensor;
    etching a cavity through the substrate, the cavity having substantially parallel interior walls; and removing a portion of the etch stop layer between the cavity and the membrane layer to expose a portion of the membrane layer.

2. The method of claim 1 further comprising the steps of etching a hole in the piezoelectric and forming a ground contact on a silicon membrane layer.

3. A method for manufacturing a flexural plate wave sensor, the method comprising the steps of:

depositing an etch-stop layer over a substrate;

depositing a membrane layer over said etch stop layer;

depositing a piezoelectric layer over said membrane layer;

forming a comb pattern on said piezoelectric layer, said comb pattern including drive and sense teeth which span an entire length of the membrane layer, the comb pattern aligned with a number of eigenmodes of the flexural plate to reduce the number of eigenmodes excited in the plate and simplify the operation and design of the flexure plate wave sensor;

forming a second transducer on said piezoelectric layer, spaced from a first transducer;

etching a cavity through the substrate, the cavity having substantially parallel interior walls;

removing the portion of the etch stop layer between the cavity and the membrane layer to expose a portion of the membrane layer; and depositing an absorptive coating on the exposed portion of the membrane layer.

4. The method of claim 3 further comprising the steps of etching a hole in the piezoelectric and forming a ground contact on a silicon membrane layer.

* * * * *